US008236772B2

(12) United States Patent
Cooke et al.

(10) Patent No.: US 8,236,772 B2
(45) Date of Patent: Aug. 7, 2012

(54) METHODS OF MODULATING ANGIOGENESIS AND SCREENING COMPOUNDS FOR ACTIVITY IN MODULATING ANGIOGENESIS

(75) Inventors: John P. Cooke, Palo Alto, CA (US); Martin Ng, Sydney (AU); Jenny C. Wu, Cupertino, CA (US); Edwin Chang, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 739 days.

(21) Appl. No.: 11/521,787

(22) Filed: Sep. 15, 2006

(65) Prior Publication Data

US 2007/0135369 A1    Jun. 14, 2007

Related U.S. Application Data

(60) Provisional application No. 60/718,113, filed on Sep. 16, 2005.

(51) Int. Cl.
*C12N 15/11*  (2006.01)
*A61K 48/00*  (2006.01)
*C07H 21/04*  (2006.01)
*A01N 63/00*  (2006.01)

(52) U.S. Cl. .............. 514/44 A; 514/44 R; 424/93.21; 536/24.5

(58) Field of Classification Search .................. None
See application file for complete search history.

(56) References Cited

U.S. PATENT DOCUMENTS

| 2003/0199464 A1* | 10/2003 | Itescu ........................... 514/44 |
| 2004/0033495 A1 | 2/2004 | Murray et al. |
| 2005/0186179 A1* | 8/2005 | Harats et al. .................. 424/93.2 |
| 2005/0233992 A1* | 10/2005 | Itescu ........................... 514/44 |
| 2006/0122138 A1* | 6/2006 | Kinch et al. ..................... 514/44 |

OTHER PUBLICATIONS

Naggy et al 2003; Trends Cardiovac Med. 13:169-175.*
Aranda et al., 2005, Investigative Ophthalmol. & Visual Sci. 46:2947-2953.*
McManus et al., 2002, Nature Reviews/Genetics 3:737-747.*
Berra et al., 2003, EMBO J. 22:4082-4090.*
Cheng et al., 2002, Molecular Cancer Research 1:2-11.*
Landen et al., 2005, Cancer Research 65:6910-6918.*
Griffioen, A., et al. Tumor angiogenesis is accompanied by a decreased inflammatory response of tumor-associated endothelium. Blood. 1996, vol. 88, No. 2, pp. 667-673.
Zeng, Z., et al. 5(S)-hydroxyeicosatetraenoic acid stimulates DNA synthesis in human microvascular endothelial cells via activation of Jak/STAT and phosphatidylinositol 3-kinase/Akt, leading to induction of expression of basic fibroblast growth factor 2. Journal of Biological Chemistry. 2002, vol. 277, No. 43, pp. 41213-41219.

(Continued)

*Primary Examiner* — Robert M Kelly
*Assistant Examiner* — Kelaginamane T Hiriyanna
(74) *Attorney, Agent, or Firm* — Paula A. Borden; Bozicevic, Field & Francis LLP.

(57) ABSTRACT

The present invention provides methods of modulating angiogenesis in an individual, as well as methods of identifying a candidate agent that modulates angiogenesis, where such methods involve modulating and identifying agents that modulate expression of gene products of a subset of genes concordantly-regulated by agonists of nicotinic acetylcholine receptor (nAChR), bFGF receptor, and VEGF receptor.

5 Claims, 12 Drawing Sheets
(3 of 12 Drawing Sheet(s) Filed in Color)

OTHER PUBLICATIONS

Authors not listed, "Cholinergic regulation of growth factor-induced endothelial cell migration," Abstract presented at the Vascular Biology and Medicine meeting, Chicago, Jun. 16-19, 2005; published in Vascular Medicine 2005 10(2):136.

Wu, J., et al., "Thioredoxin regulates growth factor-induced endothelial cell migration," Abstract presented at the Vascular Biology and Medicine meeting, Chicago, Jun. 16-19, 2005; published in Vascular Medicine 2005 10(2):165.

Auerbach, R., et al., "Angiogenesis assays: A critical overview," (2003) Clinical Chemistry, 49(1):32-40.

Heeschen, C., et al., "A novel angiogenic pathway mediated by non-neuronal nicotinic acetylcholine receptors," (2002) The Journal of Clinical Investigation, 110(4):527-536.

Heeschen, C., et al., "Nicotine stimulates angiogenesis and promotes tumor growth and atherosclerosis," (2001) Nature Medicine, 7(7):833-839.

Jacobi, J., et al., "Nicotine accelerates angiogenesis and wound healing in genetically diabetic mice," (2002) American Journal of Pathology, 161(1):97-104.

Lindstrom, J., "Nicotinic acetylcholine receptors in health and disease," (1997) Molecular Neurobiology, 15:193-222.

Macklin, K., et al., "Human vascular endothelial cells express functional nicotinic acetylcholine receptors," (1998) The Journal of Pharmacology and Experimental Therapeutics, 287(1):435-439.

Parnavelas, J., et al., "Ultrastructural localization of choline acetyltransferase in vascular endothelial cells in rat brain," (1985) Nature, 316:724-725.

Sharma, G., et al., "Nicotinic receptor signaling in nonexcitable cells," (2002) The Journal of Neurobiology, 53:524-534.

Zhu, B., et al., "Second hand smoke stimulates tumor angiogenesis and growth," (2003) Cancer Cell, 4:191-196.

Dunn, et al. "Angiogenic Disturbances in Vascular and Cardiac Pathologies", *Circulation*, 2009, 120:S1142.

Ng, et al. "A Central Role for Nicotinic Cholinergic Regulation of Growth Factor-Induced Endothelial Cell Migration", *Arteriosclerosis, Thrombosis, and Vascular Biology*, 2007, 27:106-112.

\* cited by examiner

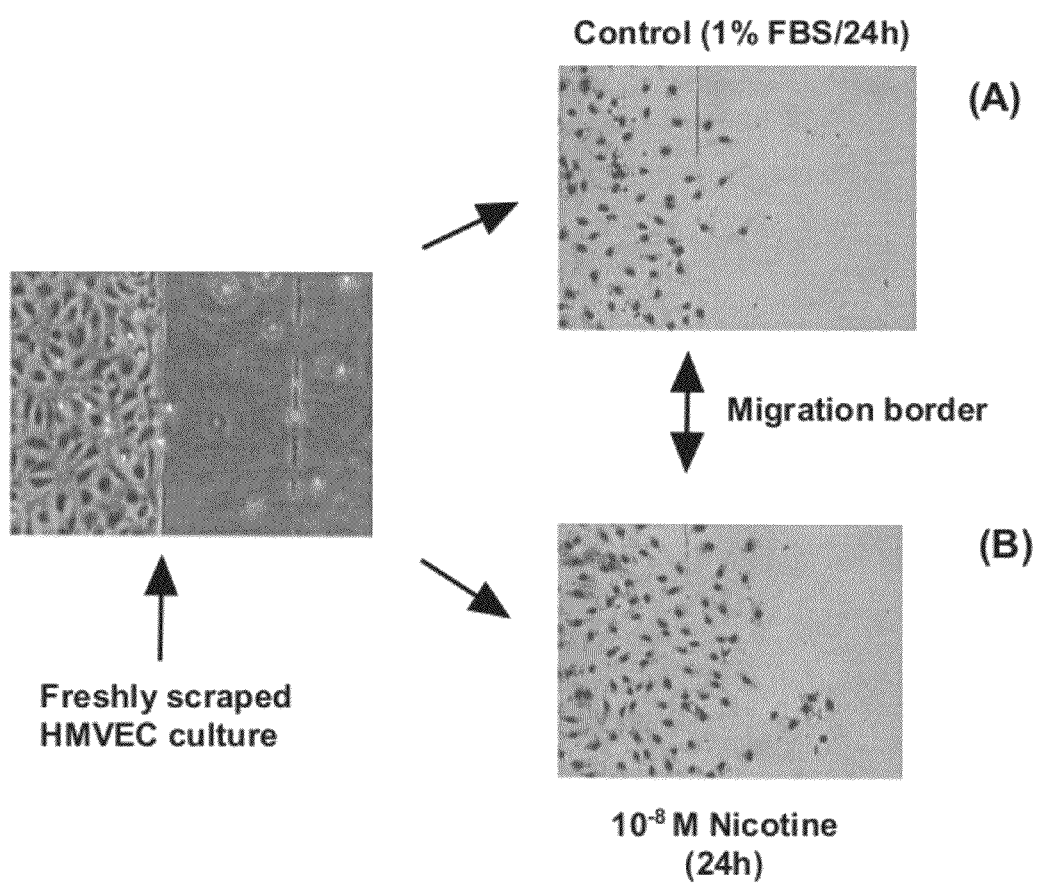

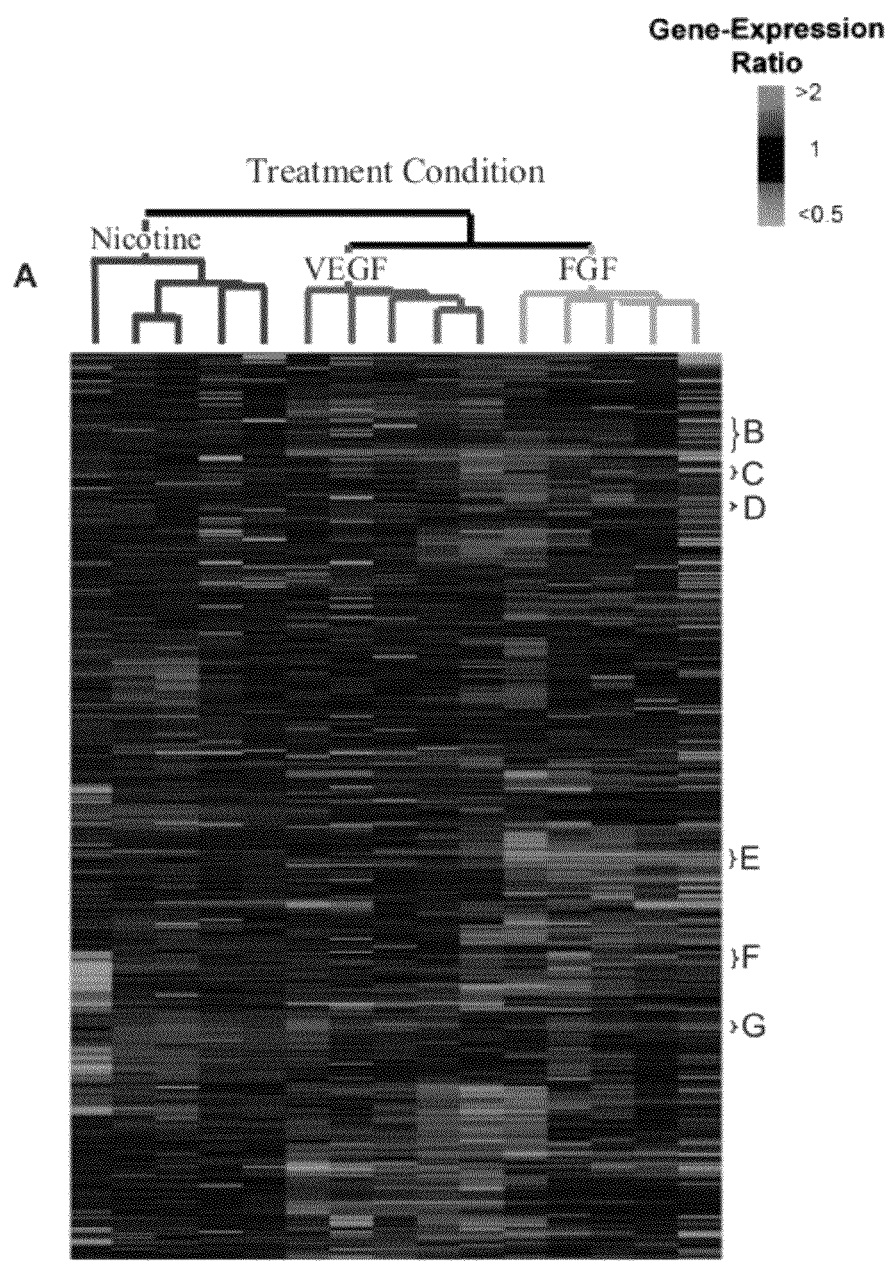

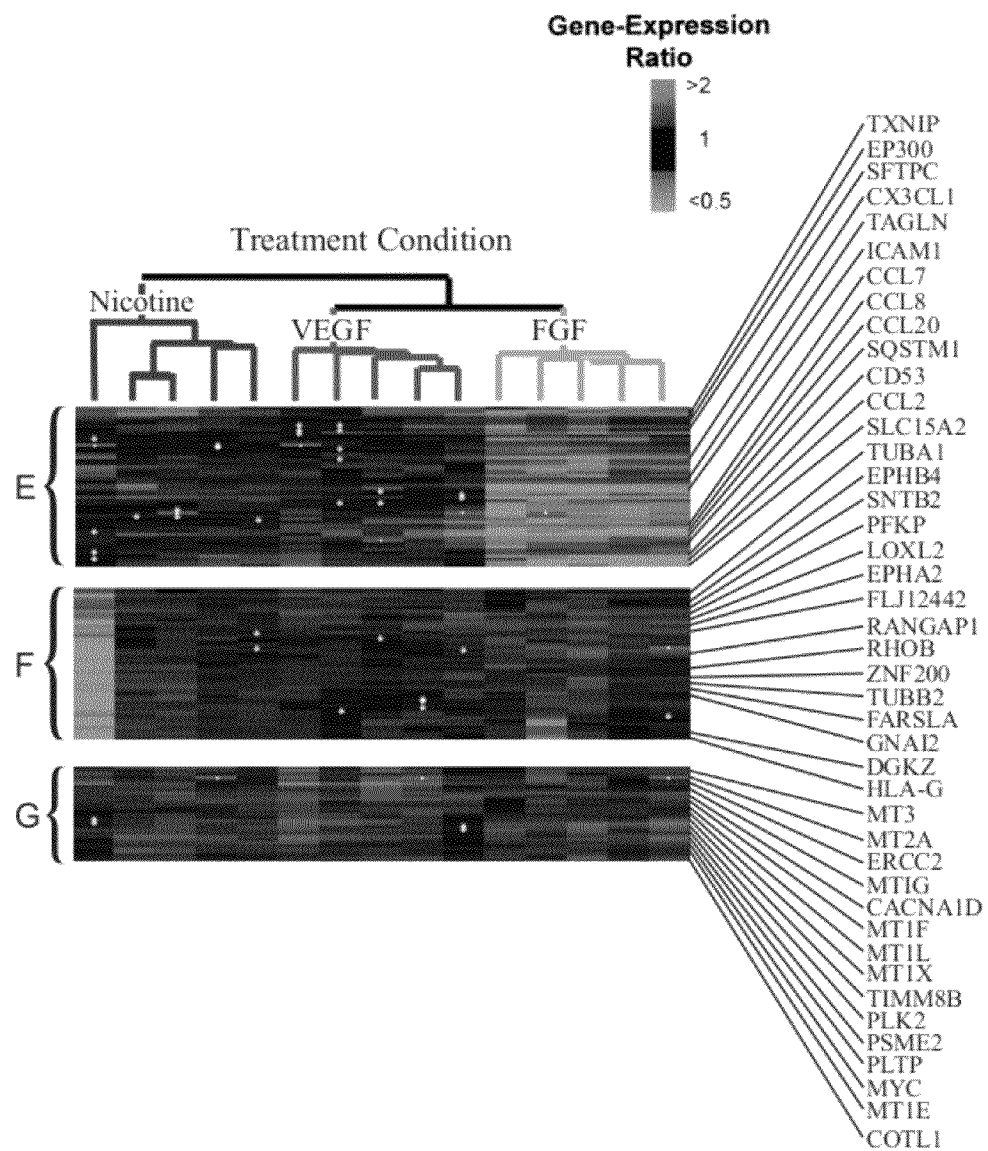

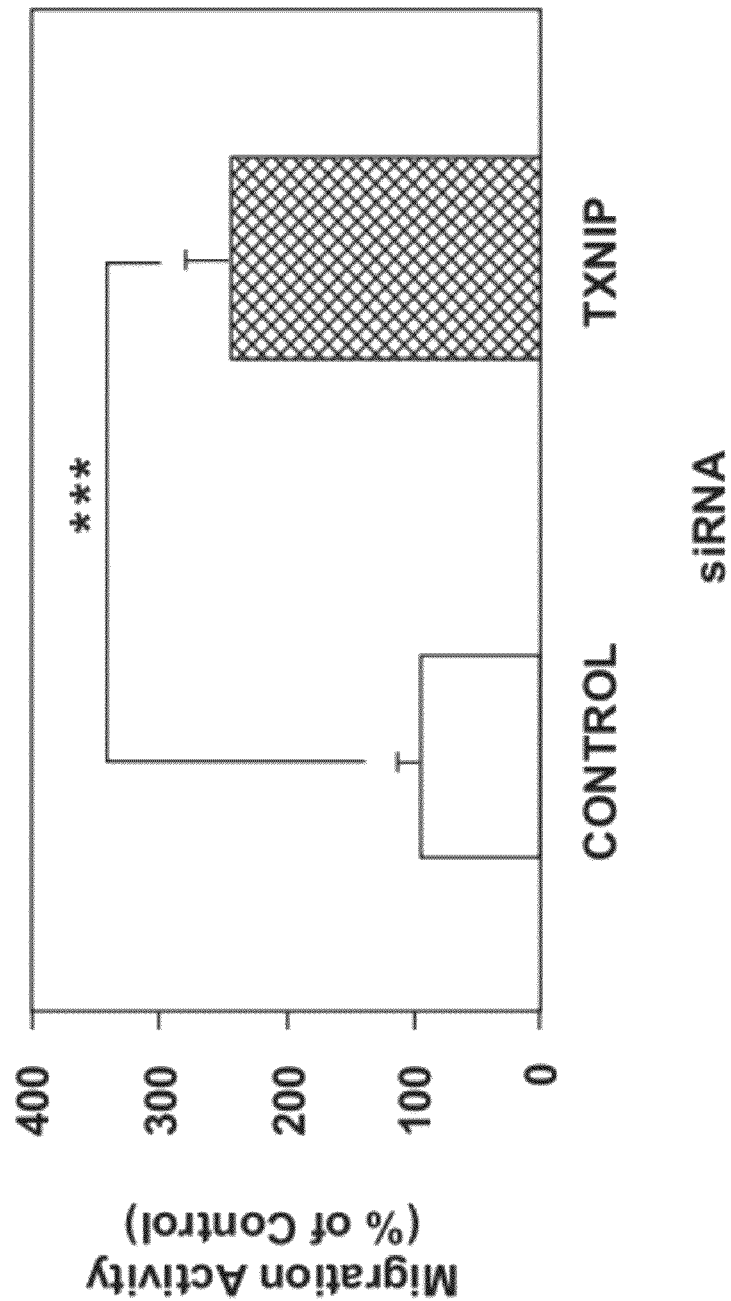

METHODS OF MODULATING ANGIOGENESIS AND SCREENING COMPOUNDS FOR ACTIVITY IN MODULATING ANGIOGENESIS

CROSS-REFERENCE TO RELATED APPLICATION

This application claims priority benefit of U.S. provisional application Ser. No. 60/718,113, filed Sep. 16, 2005, which application is incorporated herein by reference in its entirety.

STATEMENT REGARDING FEDERALLY SPONSORED RESEARCH

The U.S. government has certain rights in this invention, pursuant to grant nos. RO1 HL63685, RO1 HL075774, P01 AG18784; and PO1 AI50153 awarded by the National Institutes of Health.

FIELD OF THE INVENTION

The present application is in the field of angiogenesis, and genes differentially regulated during angiogenesis.

BACKGROUND OF THE INVENTION

The nicotinic acetylcholine receptor (nAChR) is a pentameric protein that forms a ligand-gated cationic channel. Lindstrom. (1997) *Mol Neurobiol* 15:193-222; Sharma and Vijayaraghavan (2002) *J Neurobiol* 53:524-534. The nAChR was first described in neurons, but has recently been identified in many cell types including endothelial cells (EC) and vascular smooth muscle cells. Macklin et al. (1998) *J Pharmacol Exp Ther.* 287:435-439. Intriguingly, ECs also synthesize and store acetylcholine. Parnavelas et al. (1985) *Nature* 316:724-725. Recently, it was discovered that nAChR activation causes ECs to form capillary tubes in vitro, and promotes angiogenesis in vivo. Heeschen et al. (2001) *Nat Med* 7:833-839; and Heeschen et al. (2002) *J. Clin. Invest.* 110:527-536.

Activation of the EC nAChR stimulates pathological neovascularization. Nicotine accelerates tumor angiogenesis and tumor growth in a murine Lewis lung cancer model. Heeschen et al. (2001) supra. The acceleration of tumor growth by environmental tobacco smoke is also mediated by nAChR-induced angiogenesis. Zhu et al. (2003) *Cancer Cell* 4:191-196. Furthermore, nAChR activation by nicotine stimulates the neovascularization and progression of atherosclerotic plaque. Heeschen et al. (2001) supra. Physiological as well as pathological angiogenesis can be mediated by this receptor. Activation, of the nAChR in a murine model of diabetic ulceration enhances wound angiogenesis and healing. Jacobi et al. (2002) *Am J Pathol.* 161:97-104. To date, the mechanisms of nAChR-mediated angiogenesis and their relationship to established angiogenic growth factors, such as VEGF and bFGF, are unknown.

Angiogenesis and vasculogenesis are processes involved in the growth of blood vessels. Angiogenesis is the process by which new blood vessels are formed from extant capillaries, while vasculogenesis involves the growth of vessels deriving from endothelial progenitor cells. Angiogenesis and vasculogenesis, and the factors that regulate these processes, are important in embryonic development, inflammation, and wound healing, and also contribute to pathologic conditions such as tumor growth, diabetic retinopathy, rheumatoid arthritis, and chronic inflammatory diseases.

There is a need in the art for methods of modulating angiogenesis, and methods of identifying agents that modulate angiogenesis.

SUMMARY OF THE INVENTION

The present invention provides methods of modulating angiogenesis in an individual, as well as methods of identifying a candidate agent that modulates angiogenesis, where such methods involve modulating and identifying agents that modulate expression of gene products of a subset of genes concordantly-regulated by agonists of nicotinic acetylcholine receptor (nAChR), bFGF receptor, and VEGF receptor.

In one aspect, the methods disclosed herein generally involve administering to an individual an agent that modulates the expression of a concordantly-regulated angiogenesis-modulating gene (or "CRAM" gene).

In one embodiment, the methods of the present disclosure relate to promoting therapeutic angiogenesis by enhancing activity of a concordantly-regulated pro-angiogenic gene, and/or by repressing activity of a concordantly-regulated anti-angiogenic gene, which methods may be carried out in conjunction with administration of one or more pro-angiogenic agents, such as an angiogenic growth factor, such as fibroblast growth factor or vascular endothelial growth factor or nAChR agonist. In another embodiment, the methods of the present disclosure relate to inhibiting pathological angiogenesis by enhancing activity of a concordantly-regulated anti-angiogenic gene, and/or by repressing activity of a concordantly-regulated pro-angiogenic gene, which methods may be carried out in conjunction with administration of one or more other anti-angiogenic agents.

In one aspect, methods of reducing angiogenesis in an individual generally involve administering to an individual an agent in an amount sufficient to increase expression of a concordantly-regulated anti-angiogenic gene, wherein said administering provides for reduction of angiogenesis in the individual. In specific embodiments the concordantly-regulated anti-angiogenic gene is selected from TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, and PSME2.

In another aspect methods of reducing angiogenesis in an individual generally involves administering to an individual an agent in an amount sufficient to reduce expression of a concordantly-regulated pro-angiogenic gene, wherein said administering provides for reduction of angiogenesis in the individual. In specific embodiments, the concordantly-regulated pro-angiogenic gene is selected from RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, and PDE6G.

In embodiments related to each of the above aspects, the agent reduces angiogenesis associated with a disorder selected from tumor growth, atherosclerosis, diabetic retinopathy, age-related maculopathy, and retrolental fibroplasia. In still further embodiments related to each of the above aspects, the agent is administered by a route selected from intravenous, in or around a solid tumor, systemic, intraarterial, intraocular, and topical.

Another aspect featured by the invention is a method of stimulating angiogenesis in an individual by administering to an individual an agent in an amount sufficient to increase expression of a concordantly-regulated pro-angiogenic gene, wherein said administering provides for stimulation of angiogenesis in the individual. In related embodiments, the concordantly-regulated pro-angiogenic gene is RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G.

In another aspect the invention features a method of stimulating angiogenesis in an individual by administering to an individual an agent in an amount sufficient to decrease expression of a concordantly-regulated anti-angiogenic gene, wherein said administering provides for stimulation of angiogenesis in the individual. In related embodiments, the concordantly-regulated anti-angiogenic gene is TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2.

In embodiments related to methods of stimulating angiogenesis, the agent can be administered in an amount effective to stimulate angiogenesis in or around a wound, in or around an ulcer, in or around a skin graft, in or around a transplanted tissue, or in or around a reattached limb, where the agent can be administered by intravenous, intra-arterial, intra-pericardial, systemic, subcutaneous, intramuscular, by inhalation, topical, or transdermal delivery.

As noted above, the present disclosure also provides a method of identifying a candidate agent that modulates angiogenesis, e.g., by modulating expression of a gene product of a concordantly-regulated angiogenesis-modulating gene. The methods for identifying candidate agents that have pro-angiogenic or anti-angiogenic activity are generally carried out by contacting a cell with a candidate agent, wherein the cell expresses one or more concordantly-regulated angiogenesis-modulating genes (i.e., one or more concordantly-regulated pro-angiogenic genes and/or one or more concordantly-regulated anti-angiogenic genes); and assessing the effect of the candidate agent upon expression of the gene product.

The screening methods include identifying candidate agents that affect expression of a concordantly-regulated angiogenesis-modulating gene in a cell, i.e., a concordantly-regulated pro-angiogenic gene and/or a concordantly-regulated anti-angiogenic gene. A candidate agent that modulates angiogenesis can be identified by contacting a cell with a candidate agent, wherein the cell expresses one or more concordantly-regulated angiogenesis-modulating genes; and assessing the effect of the candidate agent upon expression of the one or more concordantly-regulated angiogenesis-modulating genes; wherein a statistically significant change in expression of the one or more concordantly-regulated angiogenesis-modulating genes in the presence of the candidate agent relative to a level of expression of the gene in the absence of the candidate agent is indicative of activity of the candidate agent in modulating angiogenesis.

In certain embodiments, the one or more concordantly-regulated angiogenesis-modulating genes are one or more concordantly-regulated pro-angiogenic genes which can be one or more of RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G. An increase in expression of a concordantly-regulated pro-angiogenic gene in the presence of the candidate agent relative to a level of expression of the gene in the absence of the candidate agent indicates the candidate agent has pro-angiogenic activity and a decrease in expression of a concordantly-regulated pro-angiogenic gene in the presence of the candidate agent relative to a level of expression of the gene in the absence of the candidate agent indicates the candidate agent has anti-angiogenic activity.

In other embodiments, the one or more concordantly-regulated angiogenesis-modulating genes includes one or more concordantly-regulated anti-angiogenic genes, wherein the one or more concordantly-regulated anti-angiogenic genes can be one or more of: TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2. An increase in expression of a concordantly-regulated anti-angiogenic gene in the presence of the candidate agent relative to a level of expression of the gene in the absence of the candidate agent indicates the candidate agent has anti-angiogenic activity and a decrease in expression of a concordantly-regulated anti-angiogenic gene in the presence of the candidate agent relative to a level of expression of the gene in the absence of the candidate agent indicates the candidate agent has pro-angiogenic activity.

The screening methods can be applied to especially screen for candidate agents that modulate expression of a concordantly-regulated angiogenesis-modulating gene. For example, the screening methods can be used to identify candidate agents that inhibit angiogenesis, where a decrease in expression of the concordantly-regulated pro-angiogenic gene in the presence of the candidate agent (e.g., relative to a level of gene expression in the absence of the candidate agent) indicates the candidate agent has activity in reducing angiogenic activity. The screening methods can also be applied to identify candidate agents that enhance angiogenesis, where an increase in expression of the concordantly-regulated pro-angiogenic gene in the presence of the candidate agent (e.g., relative to a level of gene expression in the absence of the candidate agent) indicates the candidate agent has activity in increasing angiogenic activity. Concordantly-regulated pro-angiogenic genes of interest include RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G.

The screening methods can be similarly applied to especially screen for candidate agents that modulate expression of a concordantly-regulated anti-angiogenic gene. For example, the screening methods can be used to identify a candidate agent that reduces angiogenesis, where an increase in expression of the concordantly-regulated anti-angiogenic gene in the presence of the candidate agent (e.g., relative to a level of expression of the gene in the absence of the candidate agent) indicates the candidate agent has activity in reducing angiogenic activity. The screening methods can be used to identify a candidate agent that promotes angiogenesis, where a decrease in expression of the concordantly-regulated anti-angiogenic gene in the presence of the candidate agent (e.g., relative to a level of expression of the gene in the absence of the candidate agent) indicates the candidate agent has activity in promoting angiogenic activity. Concordantly-regulated anti-angiogenic genes of interest include TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2.

Also provided are methods of screening a candidate agent for activity in promoting angiogenesis, the method comprising contacting a cell with a candidate agent, wherein the cell expresses one or more concordantly-regulated pro-angiogenic genes or one or more concordantly-regulated anti-angiogenic genes; and assessing the effect of the candidate agent upon expression of the one or more concordantly-regulated pro-angiogenic genes or the one or more concordantly-regulated anti-angiogenic genes; wherein an increase in expression of the one or more concordantly-regulated pro-angiogenic genes, and/or a decrease in expression of the one or more concordantly-regulated anti-angiogenic genes, in the presence of the candidate agent relative to a level of expression of the gene in the absence of the candidate agent indicates the candidate agent has activity in promoting angiogenesis.

In specific examples of such methods of screening for angiogenesis-promoting agents, the one or more concordantly-regulated pro-angiogenic genes is RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G. In further examples, the one or more concordantly-regulated anti-angiogenic genes is TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2.

Also provided are methods of screening a candidate agent for activity in inhibiting angiogenesis, the method comprising contacting a cell with a candidate agent, wherein the cell expresses one or more concordantly-regulated pro-angiogenic genes or one or more concordantly-regulated anti-angiogenic genes; and assessing the effect of the candidate agent upon expression of the one or more concordantly-regulated pro-angiogenic genes or the one or more concordantly-regulated anti-angiogenic genes; wherein a decrease in expression of the one or more concordantly-regulated pro-angiogenic genes, and/or a increase in expression of the one or more concordantly-regulated anti-angiogenic genes, in the presence of the candidate agent relative to a level of expression of the gene in the absence of the candidate agent indicates the candidate agent has activity in inhibiting angiogenesis In specific examples, the one or more concordantly-regulated pro-angiogenic genes is RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC 1, or PDE6G. In further examples the one or more concordantly-regulated anti-angiogenic genes is TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2.

The screening methods can also be applied to determine a concordantly-regulated angiogenesis-modulating gene expression profile, which profile is indicative of the candidate agents angiogenic or anti-angiogenic activity. Such methods generally involve obtaining a concordantly-regulated angiogenesis-modulating gene expression profile from a cell contacted with a candidate agent; and comparing said obtained expression profile to a reference concordantly-regulated angiogenesis-modulating gene expression profile to determine whether the candidate agent has activity in promoting or inhibiting angiogenesis.

The concordantly-regulated angiogenesis-modulating gene expression profile can include a dataset obtained from two or more concordantly-regulated pro-angiogenic genes of RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G; and/or can include a dataset obtained from two or more concordantly-regulated anti-angiogenic genes of TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2. In some examples, the dataset includes two or more concordantly-regulated pro-angiogenic genes and at least two or more concordantly-regulated anti-angiogenic genes.

In specific examples, the disclosure provides methods of identifying a candidate agent that modulates angiogenesis by contacting a cell with a candidate agent; and assessing the effect of the candidate agent on expression of one or more concordantly-regulated angiogenesis-modulating genes, wherein said assessing provides an angiogenesis regulatory gene expression profile. A candidate agent that elicits an anti-angiogenic regulatory gene expression profile having increased expression of a concordantly-regulated anti-angiogenic gene and/or decreased expression of a concordantly-regulated pro-angiogenic gene in the presence of the candidate agent (e.g., relative to a level of expression of the gene(s)

in the absence of the candidate agent) indicates the candidate agent has activity in reducing angiogenesis. A candidate agent that elicits an pro-angiogenic regulatory gene expression profile is one that has having decreased expression of a concordantly-regulated anti-angiogenic gene and/or increased expression of a concordantly-regulated pro-angiogenic gene in the presence of the candidate agent (e.g., relative to a level of expression of the gene(s) in the absence of the candidate agent), indicating the candidate agent has activity in enhancing angiogenesis.

The concordantly-regulated angiogenesis-modulating genes of particular interest in such angiogenic and/or anti-angiogenic gene expression profile include one or more concordantly-regulated anti-angiogenic genes selected from TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, and PSME2. The concordantly-regulated angiogenesis-modulating genes of particular interest in such angiogenic and/or anti-angiogenic gene expression profile include one or more concordantly-regulated pro-angiogenic genes selected from RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, and PDE6G.

The disclosure further provides kits, which find particular use in screening a candidate agent for activity in modulation of angiogenesis, which kits include a set of primers specific for two or more concordantly-regulated pro-angiogenic genes or two or more concordantly-regulated anti-angiogenic genes. Such kits can further include a software package for statistical analysis of concordantly-regulated angiogenesis-modulating gene expression profiles, and a reference dataset for at least one of a nAChR modulator (e.g., nAChR agonist or nAChR antagonist), a bFGF receptor modulator (e.g., bFGF), and or VEGF receptor modulator (e.g., VEGF).

The present disclosure further provides nucleic acid arrays comprising a plurality of nucleic acid probes that specifically hybridize to genes that are concordantly regulated by a nicotinic acetylcholine receptor agonist, and angiogenic growth factors such as fibroblast growth factor or vascular endothelial growth factor. In general, these arrays of polynucleotide probes generally include a support with at least one surface and a plurality of different polynucleotide probes, wherein each different polynucleotide probe hybridizes under stringent hybridization conditions to a gene product of a set of concordantly-regulated angiogenesis-modulating genes, which concordantly-regulated angiogenesis-modulating genes exhibit concordant expression in a cell when the cell is contacted with a nicotinic acetylcholine receptor agonist, a vascular endothelial growth factor receptor agonist, or basic fibroblast growth factor receptor agonist.

Genes of particular interest for such arrays include one or more concordantly-regulated anti-angiogenic genes such as TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2. Further genes of interest for such arrays include one or more concordantly-regulated pro-angiogenic genes such as a gene encoding RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G.

Such arrays can be included in a kit, and may optionally include a software package for statistical analysis of concordantly-regulated angiogenesis-modulating gene expression profiles, and a reference dataset for at least one of a nAChR modulator (e.g., nAChR agonist or nAChR antagonist), a bFGF receptor modulator (e.g., bFGF), and or VEGF receptor modulator (e.g., VEGF).

These and other aspects and features of the invention will be readily apparent to the ordinarily skilled artisan upon reading the present specification.

BRIEF DESCRIPTION OF THE DRAWINGS

The patent or application file contains at least one drawing executed in color. Copies of this patent or application publication with color drawing(s) will be provided by the U.S. Patent and Trademark Office upon request and payment of necessary fee.

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1, Panels A and B are microphotographs showing an in vitro model of endothelial cell (EC) migration.

FIGS. 3A-3C depict a hierarchical cluster analysis of genes upregulated or downregulated by nicotine, VEGF or bFGF in human microvascular endothelial cells at 24 hours. FIG. 3A, Panel A indicates the relative position of Panels B-D and Panels E-G, which are re-presented in FIGS. 3B-3C, respectively.

FIGS. 6A-B depict the effect of gene knockdown of thioredoxin interacting protein (TXNIP) on human microvascular endothelial cell (HMVEC) thioredoxin activity and cell migration.

DEFINITIONS

Figure 2A:
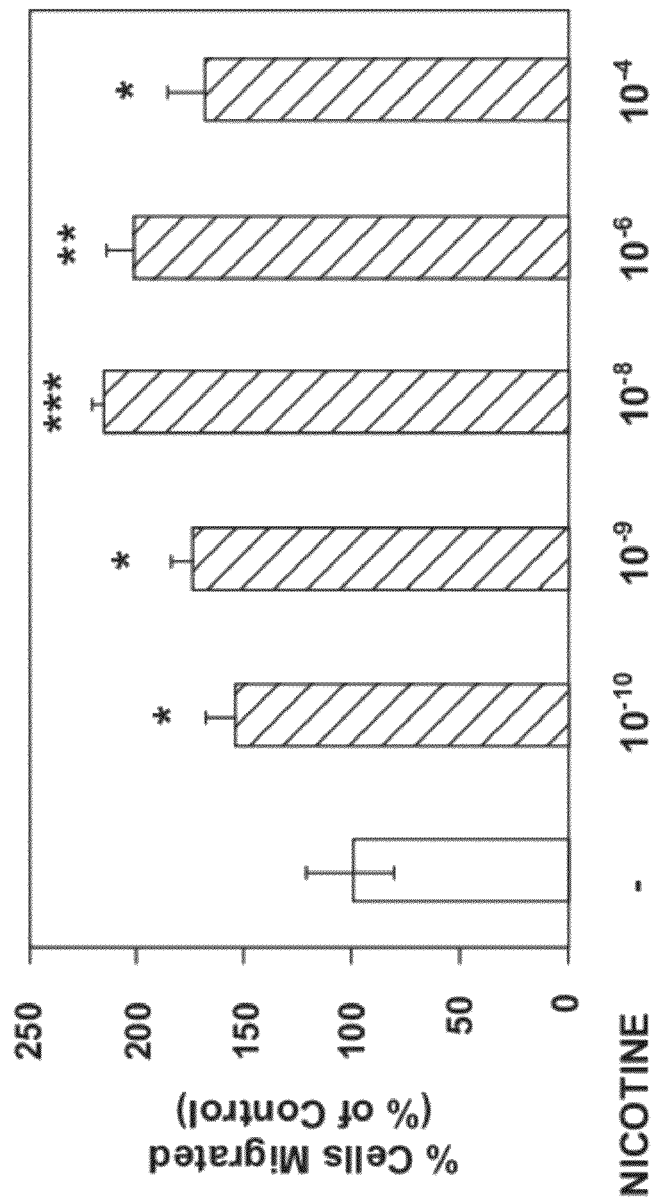
FIGS. 2A-B illustrate that the nicotinic acetylcholine receptor (nAChR) is involved in EC migration.

The term "nicotinic acetylcholine receptor" (nACh receptor) refers to a pentameric receptor, comprising 5 subunits organized symmetrically about a central ion channel, which receptor is gated by acetylcholine or by nicotine. See, e.g., Schapira et al. (2002) *BMC Structural Biology* 2:1.

"Concordant expression" or "concordantly regulated expression" refers to a phenomenon where expression of a gene is similarly affected by different stimuli that are separately applied. For example, a gene is concordantly up-regulated in expression where the gene exhibits enhanced expression under each of a selected set of stimuli to which a cell containing the gene is separately exposed. A gene is concordantly down-regulated in expression where the gene exhibits decreased expression under each of a selected set of stimuli to which a cell containing the gene is separately exposed, where an increase or decrease in gene expression is relative to an expression level of the gene in the absence of the stimuli.

By "concordantly-regulated angiogenesis gene" is meant a gene encoding a gene product that exhibits concordantly regulated expression (i.e., these genes are similarly up- or down-regulated) following exposure of a cell to a nicotinic acetylcholine receptor (nAChR) agonist (e.g., nicotine), a basic fibroblast growth factor (bFGF) receptor agonist (e.g., bFGF), and a vascular endothelial growth factor (VEGF) receptor agonist (e.g., VEGF), where the cell is separately exposed to each of these classes of stimuli. "Concordantly-regulated angiogenesis-modulating genes" include genes encoding a gene product that, when expressed, facilitates an increase in angiogenesis (i.e., a pro-angiogenic gene) and genes encoding a gene product that, when expressed, facilitates a decrease in angiogenesis (i.e., an anti-angiogenic gene).

A "concordantly-regulated pro-angiogenic gene" is a gene that encodes a gene product that promotes angiogenesis, and which exhibits expression that is concordantly up-regulated following exposure of a cell to a nicotinic acetylcholine receptor (nAChR) agonist (e.g., nicotine), a basic fibroblast growth factor (bFGF) and a vascular endothelial growth factor (VEGF), where the cell is separately exposed to each of these angiogenic stimuli, and where the gene is increased in expression in response to exposure of the cell to each of these three stimuli relative to an expression level of the gene in the absence of these stimuli.

A "concordantly-regulated anti-angiogenic gene" encodes a gene product that inhibits angiogenesis, and which exhibits expression that is concordantly down-regulated following exposure of a cell to a nicotinic acetylcholine receptor (nAChR) agonist (e.g., nicotine), a basic fibroblast growth factor (bFGF) receptor agonist (e.g., bFGF), and a vascular endothelial growth factor (VEGF) receptor agonist (e.g., VEGF), where the cell is separately exposed to each of these angiogenic stimuli, and where the gene is reduced in expression in response to separate exposure of the cell to each of these three stimuli relative to an expression level of the gene in the absence of these stimuli.

As used throughout, "modulation" is meant to refer to an increase or a decrease in the indicated phenomenon (e.g., modulation of a biological activity refers to an increase in a biological activity or a decrease in a biological activity). Accordingly, a "modulator" in reference to a receptor, refers to a compound that facilitates an increase or decrease in activity of the recited receptor (e.g., a nAChR agonist or antagonist).

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50 C or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines, simians, humans, felines, canines, equines, bovines, mammalian farm animals, mammalian sport animals, and mammalian pets.

As used herein, the term "determining" refers to both quantitative and qualitative determinations and as such, the term "determining" is used interchangeably herein with "assaying," "measuring," and the like.

The term "nicotinic acetylcholine receptor agonist" (nAChR agonist) is meant to encompass nicotine (which has the chemical name S-3-(1-methyl-2-pyrrolidinyl)pyridine; and which is understood to include nicotine derivatives and like compounds, and salts thereof) and other compounds that substantially specifically bind a nicotinic acetylcholine receptor and provide a pharmacological effect, e.g., induction of angiogenesis. nAChR agonists encompass naturally-occurring compounds (including, but not limited to, small molecules, polypeptides, peptides, etc., particularly naturally-occurring plant alkaloids, and the like), endogenous ligands (e.g., purified from a natural source, recombinantly produced, or synthetic, and further including derivatives and variants of such endogenous ligands), and synthetically produced compounds (e.g., small molecules, peptides, etc.). Also included in the definition of "nAChR agonist" are choline esterase inhibitors, which reduce the degradation of endogenous acetylcholine, thereby increasing activation of the nACh receptor. Salts of the foregoing molecules, particularly pharmaceutically acceptable salts, are also included as nAChR agonists.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an concordantly-regulated angiogenesis-modulating gene" includes a plurality of such genes and reference to "the array" includes reference to one or more array and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. For example, any positively recited element of the disclosure provides basis for a negative limitation to exclude that element from the claims. For example, where a gene is recited in a list of genes, the recited genes may be positively included (e.g., by way of recitation of a generic term encompassing the gene or specific recitation of the gene) or specifically excluded (e.g., recitation of TXNIP provides basis for a proviso excluding TXNIP, e.g., where the concordantly-regulated angiogenesis-modulating gene is other than TXNIP).

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides methods of modulating angiogenesis in an individual, as well as methods of identifying a candidate agent that modulates angiogenesis, where such methods involve modulating and identifying agents that modulate expression of gene products of a subset of genes concordantly-regulated by agonists of nicotinic acetylcholine receptor (nAChR), bFGF receptor, and VEGF receptor.

The present disclosure thus provides methods of modulating angiogenesis in an individual, the methods generally involving administering to a mammal an agent (e.g., an individual gene, a protein product of said gene, or an agent that modulates the expression of a gene), where the gene is one of a subset of concordantly-regulated angiogenesis-modulating genes. These methods in one aspect involve the promotion of therapeutic angiogenesis by the activation of (including the use of) concordantly-regulated pro-angiogenic genes or their products, which can be carried out in combination with angiogenic growth factors such as fibroblast growth factor or vascular endothelial growth factor. In another aspect, the methods of the invention involve the promotion of therapeutic angiogenesis by the repression of concordantly-regulated anti-angiogenic genes or their products, which can be carried out in combination with other pro-angiogenic agents, for example, angiogenic growth factors such as fibroblast growth factor or vascular endothelial growth factor or nAChR agonists.

In another aspect the methods involve inhibition of pathological angiogenesis by the activation (including use of) concordantly-regulated anti-angiogenic genes or their products, which can be carried out in combination with other anti-angiogenic agents. The invention further contemplates methods for inhibition of pathological angiogenesis by the repression of concordantly-regulated pro-angiogenic genes or their products, which can be carried out in combination with other anti-angiogenic agents.

The present disclosure further provides a method of identifying a candidate agent that modulates angiogenesis by modulating activity of a concordantly-regulated angiogenesis-modulating gene or gene product, which genes or gene products are angiogenic or anti-angiogenic. The present disclosure further provides nucleic acid arrays comprising a plurality of nucleic acid probes that specifically hybridize to genes that are concordantly regulated by a nAChR modulator (e.g., nAChR agonist (e.g., nicotine)), a bFGF receptor modulator (e.g., bFGF), and or VEGF receptor modulator (e.g., VEGF).

The present invention is based in part on the following observations. In a study of endothelial cell (EC) migration, a key event in angiogenesis, it was discovered that both VEGF-induced and bFGF-induced EC migration depends upon nAChR activitation. Nicotine stimulated EC migration, which is mediated by EC nAChRs, is abolished by nAChR antagonists (hexamethonium, α-bungarotoxin). Unexpectedly, it was found that nAChR antagonists also inhibit the effects of basic fibroblast growth factor (bFGF) or vascular endothelial growth factor (VEGF) to induce EC migration. Transcriptional profiling revealed a subset of genes that are concordantly regulated by all three stimuli. One of these concordantly regulated genes encodes thioredoxin-interacting protein (TXNIP). TXNIP is an endogenous inhibitor of the redox regulator thioredoxin. TXNIP was downregulated by nAChR activation as well as by VEGF or FGF stimulation. Furthermore, TXNIP repression subsequently increased thioredoxin activity. Notably, silencing of thioredoxin expression abrogated the effect of growth factors or nicotine on EC migration. Intriguingly, nAChR antagonism annulled the effect of growth factors (VEGF or bFGF) to induce thioredoxin activity. It was concluded that growth factor-induced EC migration requires nAChR activation, an effect which is, in part, modulated by nAChR-dependent downregulation of TXNIP activity.

Methods of Modulating Angiogenesis

The present invention provides methods of modulating angiogenesis in an individual, the methods generally involving administering to an individual a nucleic acid encoding a gene product, a protein product of such a gene; or an agent that modulates the expression of such a gene, where the gene is one of a subset of concordantly-regulated angiogenesis-modulating genes, as described herein. These methods include the therapeutic modulation or use of concordantly-regulated angiogenesis-modulating genes or their products (or other agents that provide for modulation of concordantly-regulated angiogenesis-modulating gene activity), which can further be provided as a combination therapy with other angiogenesis modulating agents (e.g., pro-angiogenic agents (e.g., angiogenic growth factors such as fibroblast growth factor, vascular endothelial growth factor, nAChR agonists) or anti-angiogenic agents).

In the context of methods of modulating angiogenesis the term "therapeutic agent" (or "agent" as used in the context of the therapies disclosed herein) generally refers to an agent that does not mediate a pro-angiogenic or anti-angiogenic effect through direct interaction with a nAChR, bFGF receptor or VEGF receptor, and thus specifically excludes, for example, nicotine, bFGF and VEGF.

Where an increase in activity of a concordantly-regulated angiogenesis-modulating gene is desired, the agent can provide for an increase in expression of a concordantly-regulated angiogenesis-modulating gene by at least about 5%, at least about 10%, at least about 15%, at least about 25%, at least about 30%, at least about 50%, at least about 75%, at least about 2-fold, at least about 5-fold, at least about 10-fold, at least about 15-fold, at least about 20-fold, or at least about 50-fold, or more, compared to the level of expression of the gene in the absence of the agent.

Where a decrease in activity of a concordantly-regulated angiogenesis-modulating gene is desired, the agent can provide for a decrease in expression of a concordantly-regulated angiogenesis-modulating gene by at least about 5%, at least about 10%, at least about 15%, at least about 25%, at least about 30%, at least about 50%, at least about 75%, or at least about 80%, or more, compared to the level of expression of the gene in the absence of the agent.

It should be noted that where an increase or decrease in expression of a gene is referred to herein, such is relative to a level of gene expression prior to exposure to the selected agent. Furthermore, an increase in gene expression of a concordantly-regulated angiogenesis-modulating gene contemplates use of nucleic acid that encodes a gene product (e.g., polypeptide) of the concordantly-regulated angiogenesis-modulating gene.

A "concordantly-regulated pro-angiogenic gene" is a gene that encodes a gene product that promotes angiogenesis, and which exhibits expression that is concordantly up-regulated following exposure of a cell to a nicotinic acetylcholine receptor (nAChR) agonist (e.g., nicotine), a basic fibroblast growth factor (bFGF) and a vascular endothelial growth factor (VEGF), where the cell is separately exposed to each of these angiogenic stimuli, and where the gene is increased in expression in response to exposure of the cell to each of these three stimuli relative to an expression level of the gene in the absence of these stimuli. Examples of concordantly-regulated pro-angiogenic genes include, but are not limited to RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf14, CR1L, PANK3, SENP2, PEG10, RDH13, TSN, BBOX1, PAICS, MKI67, RB1CC1, and PDE6G.

A "concordantly-regulated anti-angiogenic gene" encodes a gene product that inhibits angiogenesis, and which exhibits expression that is concordantly down-regulated following exposure of a cell to a nicotinic acetylcholine receptor (nAChR) agonist (e.g., nicotine), a basic fibroblast growth factor (bFGF) receptor agonist (e.g., bFGF), and a vascular endothelial growth factor (VEGF) receptor agonist (e.g., VEGF), where the cell is separately exposed to each of these angiogenic stimuli, and where the gene is reduced in expression in response to separate exposure of the cell to each of these three stimuli relative to an expression level of the gene in the absence of these stimuli. Examples of concordantly-regulated anti-angiogenic genes include, but are not limited to, TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, and PSME2.

A therapeutic agent that increases angiogenesis by increasing expression of a concordantly-regulated pro-angiogenic gene is an agent that increases expression of one or more genes that are concordantly up-regulated in response to a nAChR agonist (e.g., nicotine), a bFGF receptor agonist (e.g., bFGF), or a VEGF receptor agonist (e.g., VEGF), with the proviso that the therapeutic agent does not mediate a pro-angiogenic effect through direct interaction with a nAChR, bFGF receptor or VEGF receptor (and thus specifically excludes, for example, nicotine, bFGF and VEGF).

Alternatively, an agent that increases angiogenesis by reducing expression of a concordantly-regulated anti-angiogenic gene is an agent that reduces expression of one or more genes that are concordantly down-regulated in response to a nAChR agonist (e.g., nicotine), a bFGF receptor agonist (e.g., bFGF), or a VEGF receptor agonist (e.g., VEGF), with the proviso that the therapeutic agent does not mediate a pro-angiogenic effect through direct interaction with a nAChR, bFGF receptor or VEGF receptor (and thus specifically excludes, for example, nicotine, bFGF and VEGF).

Whether an agent modulates expression of a concordantly-regulated angiogenesis-modulating gene is readily determined using assays designed to detect the presence and/or level of an mRNA encoded by a concordantly-regulated angiogenesis-modulating gene and/or using assays designed to detect the presence and/or level of a protein encoded by a concordantly-regulated angiogenesis-modulating gene.

The presence and/or level of an mRNA encoded by a concordantly-regulated angiogenesis-modulating gene can be determined using any of a variety of assays. To be clear, the methods of modulating angiogenesis in an individual disclosed herein do not require assessing expression levels of a concordantly-regulated angiogenesis-modulating gene, but rather involve use of an agent(s) characterized as providing for a described modulation of concordantly-regulated angiogenesis-modulating gene expression. Assessing expression levels of a concordantly-regulated angiogenesis-modulating gene can, however, optionally be included as a part of monitoring therapy where desired. A number of methods are available for analyzing nucleic acids for the presence and/or level of a specific mRNA in a cell. The mRNA may be assayed directly or reverse transcribed into cDNA for analysis. The nucleic acid may be amplified by conventional techniques, such as the polymerase chain reaction (PCR), to provide sufficient amounts for analysis. The use of PCR is described in Saiki, et al. (1985), *Science* 239:487, and a review of techniques may be found in Sambrook, et al. *Molecular Cloning: A Laboratory Manual*, CSH Press 1989, pp. 14.2-14.33. In addition, several textbooks provide details of the PCR. See, e.g., "PCR Protocols: A Guide to methods and Applications" M. Innis et al. (1989) Academic Press; and "Quantitation of mRNA by Polymerase Chain Reaction: Non-radioactive PCR Methods" T. Köhler et al. (1995) Springer.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

A variety of different methods for determining the nucleic acid abundance in a sample are known to those of skill in the art, where particular methods of interest include those described in: Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143: 298. Also of interest are the methods disclosed in WO 97/27317.

A variety of hybridization techniques can be used to determine the presence and/or level of an mRNA in a sample. A nucleic acid probe that hybridizes, e.g., under stringent hybridization conditions, to a concordantly-regulated angiogenesis-modulating gene-encoded mRNA, will in many embodiments be used. In some embodiments, the nucleic acid probe is detectably labeled, and the presence and/or level of the concordantly-regulated angiogenesis-modulating gene-encoded mRNA is indicated by the presence and/or level of detectably labeled nucleic acid probe.

In other embodiments, a cDNA copy of a concordantly-regulated angiogenesis-modulating gene-encoded mRNA is generated (e.g., using reverse transcriptase), where the cDNA copy is detectably labeled and is hybridized to a nucleic acid probe; and the presence and/or level of the concordantly-regulated angiogenesis-modulating gene-encoded mRNA is indicated by the presence and/or level of detectably labeled cDNA that hybridizes to a nucleic acid probe. In some of these embodiments, detectably labeled cDNA copies of one or more concordantly-regulated angiogenesis-modulating gene-encoded mRNA are generated and hybridized to an array of nucleic acid probes. An array of nucleic acid probes includes a plurality of nucleic acid probes, each capable of hybridizing to a different concordantly-regulated angiogenesis-modulating gene. Suitable nucleic acid arrays are described in more detail below.

Confirmation that such an agent increases angiogenesis is readily accomplished using any of a variety of assays. Examples of suitable assays include, but are not limited to, the in vivo Matrigel plug assay; the corneal neovascularization assay; the in vivo/in vitro chick chorioallantoic membrane assay; the in vitro cellular (endothelial tube formation) assay; and the organotypic (aortic ring) assay. Such assays are known in the art and are described in a variety of references, including, e.g., Auerbach et al. (2003) *Clin. Chem.* 49:1, and references cited therein; Auerbach et al. (1976) 36:3435-3440; Akhtar et al. (2002) *Angiogenesis* 5:75-80; Staton et al. (2004) *Int. J. Exp. Pathol.* 85:233-248; Blacher et al. (2001) *Angiogenesis* 4:133-142.

Therapeutic agents that modulate expression of a concordantly-regulated angiogenesis-modulating gene, and thus are useful in the treatment methods disclosed herein, include small molecules; peptides; siRNA; antisense RNA; ribozymes; intrabodies; and the like.

Small Molecule Therapeutic Agents

In some embodiments, a therapeutic agent that modulates expression of a concordantly-regulated angiogenesis-modulating gene is a small molecule, e.g., a small organic or inorganic compound having a molecular weight of more than about 50 daltons and less than about 20,000 daltons, e.g., from about 50 daltons to about 100 daltons, from about 100 daltons to about 200 daltons, from about 200 daltons to about 500 daltons, from about 500 daltons to about 1000 daltons, from about 1000 daltons to about 2500 daltons, from about 2500 daltons to about 5000 daltons, from about 5000 daltons to about 7,500 daltons, from about 7,500 daltons to about 10,000 daltons, from about 10,000 daltons to about 15,000 daltons, or from about 15,000 daltons to about 20,000 daltons. Therapeutic agents may comprise functional groups necessary for structural interaction with proteins and/or nucleic acids, e.g., hydrogen bonding, and may include at least an amine, carbonyl, hydroxyl or carboxyl group, and may contain at least two of the functional chemical groups. The therapeutic agents may comprise cyclical carbon or heterocyclic structures and/or aromatic or polyaromatic structures substituted with one or more of the above functional groups. Therapeutic agents are also found among biomolecules including peptides, saccharides, fatty acids, steroids, purines, pyrimidines, derivatives, structural analogs, salts thereof, or combinations thereof.

siNAs and Other Nucleic Acid-Based Agents

In some embodiments, modulation of angiogenesis in an individual can be accomplished through RNA interference (RNAi) by contacting a cell with a small nucleic acid molecule, such as a short interfering nucleic acid (siNA), a short interfering RNA (siRNA), a double-stranded RNA (dsRNA), a micro-RNA (miRNA), a short hairpin RNA (shRNA) molecule, or a ribozyme, or modulation of expression of a small interfering RNA (siRNA) so as to provide for decreasing levels of expression of a concordantly-regulated angiogenesis-modulating gene (e.g., through a decrease in mRNA levels and/or a decrease in polypeptide levels). siNAs and other antisense reagents described herein may inhibit gene expression through any of a variety of mechanisms, e.g. by reducing the amount of mRNA available for translation, through activation of RNAse H, or steric hindrance. One or a combination of antisense molecules may be administered, where a combination may comprise multiple different sequences.

The term "short interfering nucleic acid", "siNA", "short interfering RNA", "siRNA", "short interfering nucleic acid molecule", "short interfering oligonucleotide molecule", or "chemically-modified short interfering nucleic acid molecule" as used herein refers to any nucleic acid molecule capable of inhibiting or down regulating gene expression, for example by mediating RNA interference "RNAi" or gene silencing in a sequence-specific manner. Design of RNAi molecules when given a target gene are routine in the art. See also US 2005/0282188 (which is incorporated herein by reference) as well as references cited therein. See, e.g., Pushparaj et al. *Clin. Exp. Pharmacol. Physiol.* 2006 33(5-6):504-10; Lutzelberger et al. *Handbk. Exp. Pharmacol.* 2006 173:243-59; Aronin et al. *Gene Ther.* 2006 13(6):509-16; Xie et al. *Drug Discov. Today* 2006 11(1-2):67-73; Grunweller et al. *Curr. Med. Chem.* 2005 12(26):3143-61; and Pekaraik et al. *Brain Res. Bull.* 2005 68(1-2):115-20.

In embodiments of particular interest, an agent that modulates expression of a concordantly-regulated angiogenesis-modulating gene is an siRNA. As discussed above, siRNA mediated gene silencing involves targeting expression products of concordantly-regulated angiogenesis-modulating gene with specific double stranded concordantly-regulated angiogenesis-modulating gene-derived siRNA nucleotide sequences that are complementary to a region of a concordantly-regulated angiogenesis-modulating gene transcript, e.g., at least a 19-25 nt long segment (e.g., a 20-21 nucleotide sequence) of the concordantly-regulated angiogenesis-modulating gene transcript, which may include the 5' untranslated (UT) region, the ORF, or the 3'UT region. In some embodiments, short interfering RNAs are about 19-25 nt in length. See, e.g., PCT applications WO0/44895, WO99/32619, WO01/75164, WO01/92513, WO01/29058, WO01/89304, WO02/16620, and WO02/29858 for descriptions of siRNA technology.

Methods for design and production of siRNAs to a desired target are known in the art, and their application to a concordantly-regulated angiogenesis-modulating gene as disclosed herein for the purposes disclosed herein will be readily apparent to the ordinarily skilled artisan, as are methods of production of siRNAs having modifications (e.g., chemical modifications) to provide for, e.g., enhanced stability, bioavailability, and other properties to enhance use as therapeutics. In addition, methods for formulation and delivery of siRNAs to a subject are also well known in the art. See, e.g., U.S. Application Pub. Nos. 2005/0282188; 2005/0239731; 2005/0234232; 2005/0176018; 2005/0059817; 2005/0020525; 2004/0192626; 2003/0073640; 2002/0150936; 2002/0142980; and 2002/0120129, each of which are incorporated herein by reference.

Publicly available tools to facilitate design of siRNAs are available in the art. See, e.g., DEQOR: Design and Quality Control of RNAi (available on the internet at cluster-1.mpicbg.de/Deqor/deqor.html) and Henschel et al. *Nucleic Acids Res.* 2004 32:W113-20. DEQOR is a web-based program which uses a scoring system based on state-of-the-art parameters for siRNA design to evaluate the inhibitory potency of siRNAs. DEQOR, therefore, can help to predict (i) regions in a gene that show high silencing capacity based on the base pair composition and (ii) siRNAs with high silencing potential for chemical synthesis. In addition, each siRNA arising from the input query is evaluated for possible cross-silencing activities by performing BLAST searches against the transcriptome or genome of a selected organism. DEQOR can therefore predict the probability that an mRNA fragment will cross-react with other genes in the cell and helps researchers to design experiments to test the specificity of siRNAs or chemically designed siRNAs.

Non limiting examples of target sites for design of siRNA molecules for a concordantly-regulated angiogenesis-modulating gene are provided in the Examples below. Target sites in the open reading frame of these and other concordantly-regulated angiogenesis-modulating genes can be found within the nucleotide sequences of the genes disclosed herein, and any complementary sequences thereof. Additional target sites can be readily identified using the tools available to the ordinarily skilled artisan as discussed above.

It should be understood that the sequences provided above are the target sequences of the mRNAs encoding the target gene, and that the siRNA oligonucleotides used would comprise a sequence complementary to the target.

siNA molecules can be of any of a variety of forms. For example the siNA can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. siNA can also be assembled from two separate oligonucleotides, where one strand is the sense strand and the other is the antisense strand, wherein the antisense and sense strands are self-complementary. In this embodiment, each strand generally comprises nucleotide sequence that is complementary to nucleotide sequence in the other strand; such as where the antisense strand and sense strand form a duplex or double stranded structure, for example wherein the double stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the siNA molecule are complementary to the target nucleic acid or a portion thereof).

Alternatively, the siNA can be assembled from a single oligonucleotide, where the self-complementary sense and antisense regions of the siNA are linked by a nucleic acid-based or non-nucleic acid-based linker(s). The siNA can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof.

The siNA can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siNA molecule capable of mediating RNAi. The siRNA can also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., 2002, *Cell* 110:563-74 and Schwarz et al., 2002, *Mol. Cell,* 10: 537-68), or 5',3'-diphosphate.

In certain embodiments, the siNA molecule contains separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. In certain embodiments, the siNA molecules comprise nucleotide sequence that is complementary to nucleotide sequence of a target gene. In another embodiment, the siNA molecule interacts with nucleotide sequence of a target gene in a manner that causes inhibition of expression of the target gene.

As used herein, siNA molecules need not be limited to those molecules containing only RNA, but further encompasses chemically-modified nucleotides and non-nucleotides. In certain embodiments, the short interfering nucleic acid molecules of the invention lack 2'-hydroxy (2'-OH) containing nucleotides. siNAs do not necessarily require the presence of nucleotides having a 2'-hydroxy group for mediating RNAi and as such, siNA molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated. groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON."

siNA may be a synthetic polynucleotide which is chemically synthesized by methods known in the art (see Wagner et al. (1996), supra.) Preferred oligonucleotides are chemically modified from the native phosphodiester structure, in order to increase their intracellular stability and binding affinity. A number of such modifications have been described in the literature, which modifications alter the chemistry of the backbone, sugars or heterocyclic bases. siNAs may also be produced by expression of all or a part of the target gene sequence in an appropriate vector, where the transcriptional initiation is oriented such that an antisense strand is produced as an RNA molecule.

siNAs are generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

siNAs may have a naturally-occurring backbone chemistry or have one or backbone modification. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The β-anomer of deoxyribose may be used, where the base is inverted with respect to the natural α-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Exemplary modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Oligonucleotides having a morpholino backbone structure (Summerton, J. E. and Weller D. D., U.S. Pat. No. 5,034,506) or a peptide nucleic acid (PNA) backbone (P. E. Nielson, M. Egholm, R. H. Berg, O. Buchardt, Science 1991, 254: 1497) can also be used. Morpholino antisense oligonucleotides are amply described in the literature. See, e.g., Partridge et al. (1996) *Antisense Nucl. Acid Drug Dev.* 6:169-175; and Summerton (1999) *Biochem. Biophys. Acta* 1489:141-158.

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, siNA molecules of the invention can be used to epigenetically silence a target gene at both the post-transcriptional level or the pre-transcriptional level. In a non-limiting example, epigenetic regulation of gene expression by siNA molecules of the invention can result from siNA mediated modification of chromatin structure or methylation pattern to alter gene expression (see, e.g., Verdel et al., 2004, *Science* 303:672-6; Pal-Bhadra et al., 2004, *Science* 303:669-72; Allshire, 2002, *Science* 297:1818-9; Volpe et al., 2002, *Science* 297:1833-7; Jenuwein, 2002, *Science* 297:2215-8; and Hall et al., 2002, *Science* 297:2232-7).

siNA molecules contemplated herein can comprise a duplex forming oligonucleotide (DFO) see, e.g., WO 05/019453; and US 2005/0233329, which are incorporated herein by reference). siNA molecules also contemplated herein include multifunctional siNA, (see, e.g., WO 05/019453 and US 2004/0249178). The multifunctional siNA can comprise sequence targeting, e.g., two regions within a selected concordantly-regulated angiogenesis-modulating gene.

siNA molecules contemplated herein can comprise an asymmetric hairpin or asymmetric duplex. By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a loop region comprising about 4 to about 12 (e.g., about 4, 5, 6, 7, 8, 9, 10, 11, or 12) nucleotides, and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a cell or in vitro system (e.g. about 15 to about 30, or about 15, 16, 17, 18, 19, 20, 21, 22, 23, 24, 25, 26, 27, 28, 29, or 30 nucleotides) and a sense region having about 3 to about 25 (e.g., about 3, 4, 5, 6, 7, 8, 9, 10, 11, 12, 13, 14, 15, 16, 17, 18, 19, 20, 21, 22, 23, 24, or 25) nucleotides that are complementary to the antisense region.

Stability and/or half-life of siRNAs can be improved through chemically synthesizing nucleic acid molecules with modifications (base, sugar and/or phosphate) can prevent their degradation by serum ribonucleases, which can increase their potency (see e.g., WO 92/07065; Perrault et al., 1990 *Nature* 344:565; Pieken et al., 1991, Science 253:314; Usman et al., 1992, Trends in Biochem. Sci. 17:334; WO 93/15187; and WO 91/03162; U.S. Pat. No. 5,334,711; U.S. Pat. No. 6,300,074; and Burgin et al., supra; all of which are incorporated by reference herein, describing various chemical modifications that can be made to the base, phosphate and/or sugar moieties of the nucleic acid molecules described herein. Modifications that enhance their efficacy in cells, and removal of bases from nucleic acid molecules to shorten oligonucleotide synthesis times and reduce chemical requirements are desired.

For example, oligonucleotides are modified to enhance stability and/or enhance biological activity by modification with nuclease resistant groups, e.g., 2'-amino, 2'-C-allyl, 2'-fluoro, 2'-O-methyl, 2'-O-allyl, 2'-H, nucleotide base modifications (for a review see Usman et al., 1992, *TIBS* 17:34; Usman et al., 1994, *Nucleic Acids Symp.* Ser. 31:163; Burgin et al., 1996, *Biochem.* 35:14090). Sugar modification of nucleic acid molecules have been extensively described in the art (see WO 92/07065; Perrault et al. *Nature*, 1990, 344: 565-8; Pieken et al. *Science*, 1991, 253:314-7; Usman et al., 1992, *TIBS* 17:334-9; WO 93/15187; U.S. Pat. No. 5,334,711 and Beigelman et al., 1995, *J. Biol. Chem.*, 270:25702; WO 97/26270; U.S. Pat. No. 5,716,824; U.S. Pat. No. 5,627,053; WO 98/13526; U.S. Application Ser. No. 60/082,404, filed on Apr. 20, 1998; Karpeisky et al., 1998, *Tetrahedron Lett.*, 39:1131; Eamshaw et al., 1998, *Biopolymers (Nucleic Acid Sciences)* 48:39-55; Verma et al., 1998, *Ann. Rev. Biochem.* 67:99-134; and Burlina et al., 1997, *Bioorg. Med. Chem.* 5:1999-2010; each of which are hereby incorporated in their totality by reference herein). In view of such teachings, similar modifications can be used as described herein to modify the siNA nucleic acid molecules of disclosed herein so long as the ability of siNA to promote RNAi is cells is not significantly inhibited.

Short interfering nucleic acid (siNA) molecules having chemical modifications that maintain or enhance activity are contemplated herein. Such a nucleic acid is also generally more resistant to nucleases than an unmodified nucleic acid. Accordingly, the in vitro and/or in vivo activity should not be significantly lowered. Nucleic acid molecules delivered exogenously are generally selected to be be stable within cells at least for a period sufficient for transcription and/or translation of the target RNA to occur and to provide for modulation of production of the encoded mRNA and/or polypeptide so as to facilitate reduction of the level of the target gene product.

Production of RNA and DNA molecules can be accomplished synthetically and can provide for introduction of nucleotide modifications to provide for enhanced nuclease stability. (see, e.g., Wincott et al., 1995, *Nucleic Acids Res.* 23:2677; Caruthers et al., 1992, *Meth. Enzymol.* 211:3-19, incorporated by reference herein. In one embodiment, nucleic acid molecules of the invention include one or more (e.g., about 1, 2, 3, 4, 5, 6, 7, 8, 9, 10, or more) G-clamp nucleotides, which are modified cytosine analogs which confer the ability to hydrogen bond both Watson-Crick and Hoogsteen faces of a complementary guanine within a duplex, and can provide for enahcned affinity and specificity to nucleic acid targets (see, e.g., Lin et al., 1998, *J. Am. Chem. Soc.*, 120:8531-2). In another example, nucleic acid molecules can include one or more (e.g., about 1, 2, 3, 4, 5, 6, 7, 8, 9, 10, or more) LNA "locked nucleic acid" nucleotides such as a 2',4'-C methylene bicyclo nucleotide (see, e.g., WO 00/66604 and WO 99/14226).

siNA molecules can be provided as conjugates and/or complexes, e.g., to facilitate delivery of siNA molecules into a cell. Exemplary conjugates and/or complexes includes those composed of an siNA and a small molecule, lipid, cholesterol, phospholipid, nucleoside, antibody, toxin, negatively charged polymer (e.g., protein, peptide, hormone, carbohydrate, polyethylene glycol, or polyamine). In general, the transporters described are designed to be used either individually or as part of a multi-component system, with or without degradable linkers. These compounds can improve delivery and/or localization of nucleic acid molecules into cells in the presence or absence of serum (see, e.g., U.S. Pat. No. 5,854,038). Conjugates of the molecules described herein can be attached to biologically active molecules via linkers that are biodegradable, such as biodegradable nucleic acid linker molecules.

In general, use of RNAi to reduce a level of a particular mRNA and/or protein is based on the interfering properties of double-stranded RNA derived from the coding regions of gene. In one example of this method, complementary sense and antisense RNAs derived from a substantial portion of the concordantly-regulated angiogenesis-modulating gene are synthesized in vitro. The resulting sense and antisense RNAs are annealed in a buffer, and the double-stranded RNA introduced into the subject. See, e.g., WO99/32619. In another embodiment, dsRNA derived from concordantly-regulated angiogenesis-modulating gene is generated in vivo by simultaneous expression of both sense and antisense RNA from appropriately positioned promoters operably linked to a concordantly-regulated angiogenesis-modulating gene coding sequences in both sense and antisense orientations.

In addition to iNAs, such as siRNAs, other antisense molecules can be used to down-regulate expression of a concordantly-regulated angiogenesis-modulating gene in cells. Such other antisense compounds include ribozymes, external guide sequence (EGS) oligonucleotides (oligozymes), and other short catalytic RNAs or catalytic oligonucleotides which hybridize to the target nucleic acid and modulate its expression.

Anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense oligodeoxynucleotides with a metal complex, e.g. terpyridylCu(II), capable of mediating mRNA hydrolysis are described in Bashkin et al. (1995), *Appl. Biochem. Biotechnol.* 54:43-56.

Stimulation of Therapeutic Angiogenesis

In some embodiments, a stimulator of therapeutic angiogenesis is administered to an individual in need thereof. In these embodiments, the stimulator of angiogenesis is an active agent that increases expression of one or more concordantly-regulated pro-angiogenic genes, and increases angiogenesis. Thus, in some embodiments, the instant invention provides a method of increasing or stimulating angiogenesis in a mammal. The method generally involves administering to a mammal an active agent in an amount effective to increase expression of one or more concordantly-regulated pro-angiogenic genes, thereby increasing angiogenesis.

These embodiments also include the promotion of therapeutic angiogenesis by the repression of concordantly-regulated anti-angiogenic genes or their products in together and/or in combination with angiogenic growth factors such as fibroblast growth factor or vascular endothelial growth factor, thereby increasing angiogenesis.

An effective amount of an active agent increases angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 2-fold, at least about 5-fold, at least about 10-fold, or more, when compared to an untreated (e.g., a placebo-treated) control. Stimulation of angiogenesis is useful to treat a variety of conditions that would benefit from stimulation of angiogenesis, stimulation of vasculogenesis, increased blood flow, and/or increased vascularity.

Examples of conditions and diseases amenable to treatment according to the method of the invention related to increasing angiogenesis include any condition associated with an obstruction of a blood vessel, e.g., obstruction of an artery, vein, or of a capillary system. Specific examples of such conditions or disease include, but are not necessarily limited to, coronary occlusive disease, carotid occlusive disease, arterial occlusive disease, peripheral arterial disease, atherosclerosis, myointimal hyperplasia (e.g., due to vascular surgery or balloon angioplasty or vascular stenting), thromboangiitis obliterans, thrombotic disorders, vasculitis, and the like. Examples of conditions or diseases that can be prevented using the methods of the invention include, but are not necessarily limited to, heart attack (myocardial infarction) or other vascular death, stroke, death or loss of limbs associated with decreased blood flow, and the like.

Other forms of therapeutic angiogenesis include, but are not necessarily limited to, the use of an active agent that modulates expression of a concordantly-regulated angiogenesis-modulating gene to accelerate healing of wounds or ulcers (e.g., as a result of physical injury or disease, e.g., cutaneous ulcers, diabetic ulcers, ulcerative colitis, and the like); to improve the vascularization of skin grafts or reattached limbs so as to preserve their function and viability; to improve the healing of surgical anastomoses (e.g., as in reconnecting portions of the bowel after gastrointestinal surgery); and to improve the growth of skin or hair.

In order to accomplish stimulation of angiogenesis in vivo (e.g., as in the context of therapeutic angiogenesis), a modulator of the expression of one or more concordantly-regulated angiogenesis-modulating genes can be administered in any suitable manner, preferably with pharmaceutically acceptable carriers. One skilled in the art will readily appreciate that the a variety of suitable methods of administering an active agent in the context of the present invention to a subject are available, and, although more than one route can be used to administer a particular compound, a particular route can provide a more immediate, more effective, and/or associated with fewer side effects than another route. In general, an active agent is administered according to the method of the invention by, for example, a parenteral, intravenous, intra-arterial, inter-pericardial, intramuscular, intraperitoneal, transdermal, transcutaneous, subdermal, intradermal, or intrapulmonary route.

In some embodiments, an active agent will be delivered locally. Local administration can be accomplished by, for example, direct injection (e.g., intramuscular injection) at the desired treatment site, by introduction of the active agent formulation intravenously at a site near a desired treatment site (e.g., into a vessel or capillary that feeds a treatment site), by intra-arterial or intra-pericardial introduction, by introduction (e.g., by injection or other method of implantation) of an active agent formulation in a biocompatible gel or capsule within or adjacent a treatment site, by injection directly into muscle or other tissue in which increased blood flow and/or increased vascularity is desired, by rectal introduction of the formulation (e.g., in the form of a suppository to, for example, facilitate vascularization of a surgically created anastomosis after resection of a piece of the bowel), etc.

In some embodiments it may be desirable to deliver the active agent directly to the wall of a vessel. One exemplary method of vessel wall administration involves the use of a drug delivery catheter, particularly a drug delivery catheter comprising an inflatable balloon that can facilitate delivery to a vessel wall. Thus, in one embodiment the method of the invention comprises delivery of an active agent to a vessel wall by inflating a balloon catheter, wherein the balloon comprises an active agent formulation covering a substantial portion of the balloon. The active agent formulation is held in place against the vessel wall, promoting adsorption through the vessel wall. In one example, the catheter is a perfusion balloon catheter, which allows perfusion of blood through the catheter while holding the active agent against the vessel walls for longer adsorption times. Examples of catheters suitable for active agent application include drug delivery catheters disclosed in U.S. Pat. Nos. 5,558,642; 5,554,119; 5,591,129; and the like.

In another embodiment of interest, the active agent formulation is delivered in the form of a biocompatible gel, which can be implanted (e.g., by injection into or adjacent a treatment site, by extrusion into or adjacent a tissue to be treated, etc.). Gel formulations comprising an active agent can be designed to facilitate local release of the active agent for a sustained period (e.g., over a period of hours, days, weeks, etc.). The gel can be injected into or near a treatment site, e.g., using a needle or other delivery device. In one embodiment, the gel is placed into or on an instrument which is inserted into the tissue and then slowly withdrawn to leave a track of gel, resulting in stimulation of angiogenesis along the path made by the instrument. This latter method of delivery may be particularly desirable for, for the purpose of directing course of the biobypass.

In other embodiments it may be desirable to deliver the active agent formulation topically, e.g., for localized delivery, e.g., to facilitate wound healing. Topical application can be accomplished by use of a biocompatible gel, which may be provided in the form of a patch, or by use of a cream, foam, and the like. Several gels, patches, creams, foams, and the like appropriate for application to wounds can be modified for delivery of active agent formulations according to the invention (see, e.g., U.S. Pat. Nos. 5,853,749; 5,844,013; 5,804,213; 5,770,229; and the like). In general, topical administration is accomplished using a carrier such as a hydrophilic colloid or other material that provides a moist environment. Alternatively, for the purpose of wound healing the active agent could be supplied, with or without other angiogenic agents in a gel or cream then could be applied to the wound. An example of such an application would be as a sodium carboxymethylcellulose-based topical gel with a low bioburden containing the active agent and other active ingredients together with preservatives and stabilizers.

In other embodiments, the active agent formulation is delivered locally or systemically, preferably locally, using a transdermal patch. Several transdermal patches are well known in the art for systemic delivery of nicotine to facilitate smoking cessation, and such patches may be modified to provide for delivery of an amount of active agent effective to stimulate angiogenesis according to the invention (see, e.g., U.S. Pat. Nos. 4,920,989; and 4,943,435, NICOTROL™ patch, and the like).

In other methods of delivery, the active agent can be administered using iontophoretic techniques. Methods and compositions for use in iontophoresis are well known in the art (see, e.g., U.S. Pat. Nos. 5,415,629; 5,899,876; 5,807,306; and the like).

The desirable extent of angiogenesis will depend on the particular condition or disease being treated, as well as the stability of the patient and possible side-effects. In proper doses and with suitable administration, the present invention provides for a wide range of development of blood vessels, e.g., from little development to essentially full development.

Inhibition of Pathological Angiogenesis

In some embodiments, an inhibitor of angiogenesis is administered to an individual in need thereof. In these embodiments, an active agent that is administered to the individual increases the expression of one or more concordantly-regulated anti-angiogenic genes. Alternatively, or in addition, the active agent decreases the expression of concordantly-regulated pro-angiogenic genes. In these embodiments, the active agent reduces angiogenesis. Thus, in some embodiments, the instant invention provides a method of reducing angiogenesis in a mammal. The method generally involves administering to a mammal an active agent in an amount effective to modulate expression of one or more concordantly-regulated angiogenesis-modulating genes, thereby reducing angiogenesis. An effective amount of an active agent reduces angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or more, when compared to an untreated (e.g., a placebo-treated) control.

Whether angiogenesis is reduced can be determined using any known method. Methods of determining an effect of an agent on angiogenesis are known in the art and include, but are not limited to, inhibition of neovascularization into implants impregnated with an angiogenic factor; inhibition of blood vessel growth in the cornea or anterior eye chamber; inhibition of endothelial tube formation in vitro; the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

The invention further provides methods for treating a condition or disorder associated with or resulting from pathological angiogenesis. In the context of cancer therapy, a reduction in angiogenesis according to the methods of the invention effects a reduction in tumor size; and a reduction in tumor metastasis. Whether a reduction in tumor size is achieved can be determined, e.g., by measuring the size of the tumor, using standard imaging techniques. Whether metastasis is reduced can be determined using any known method. Methods to assess the effect of an agent on tumor size are well known, and include imaging techniques such as computerized tomography and magnetic resonance imaging.

Any condition or disorder that is associated with or that results from pathological angiogenesis, or that is facilitated by neovascularization (e.g., a tumor that is dependent upon neovascularization), is amenable to treatment with an agent that modulates the expression of concordantly-regulated angiogenesis-modulating genes so as to inhibit angiogenesis.

Conditions and disorders amenable to treatment include, but are not limited to, cancer; atherosclerosis; proliferative retinopathies such as retinopathy of prematurity, diabetic retinopathy, age-related maculopathy, retrolental fibroplasia; excessive fibrovascular proliferation as seen with chronic arthritis; psoriasis; and vascular malformations such as hemangiomas, and the like.

The instant methods are useful in the treatment of both primary and metastatic solid tumors, including carcinomas, sarcomas, leukemias, and lymphomas. Of particular interest is the treatment of tumors occurring at a site of angiogenesis. Thus, the methods are useful in the treatment of any neoplasm, including, but not limited to, carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). The instant methods are also useful for treating solid tumors arising from hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, the instant methods are useful for reducing metastases from the tumors described above either when used alone or in combination with radiotherapy and/or other chemotherapeutic agents.

Other conditions and disorders amenable to treatment using the methods of the instant invention include autoimmune diseases such as rheumatoid, immune and degenerative arthritis; various ocular diseases such as diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, and other abnormal neovascularization conditions of the eye; skin diseases such as psoriasis; blood vessel diseases such as hemangiomas, and capillary proliferation within atherosclerotic plaques; Osler-Webber Syndrome; plaque neovascularization; telangiectasia; hemophiliac joints; angiofibroma; and excessive wound granulation (keloids).

In order to accomplish reduction of angiogenesis in vivo (e.g., as in the context of treating pathological angiogenesis), a modulator of one or more concordantly-regulated angiogenesis-modulating genes will be administered in any suitable manner, typically with pharmaceutically acceptable carriers. One skilled in the art will readily appreciate that the a variety of suitable methods of administering an active agent in the context of the present invention to a subject are available, and, although more than one route can be used to administer a particular compound, a particular route can provide a more immediate, more effective, and/or associated with fewer side effects than another route. In general, an active agent can be administered according to the method of the invention by, for example, a parenteral, intratumoral, peritumoral, intravenous, intra-arterial, inter-pericardial, intramuscular, intraperitoneal, transdermal, transcutaneous, subdermal, intradermal, or intrapulmonary route.

In some embodiments, an active agent will be delivered locally. Local administration can be accomplished by, for example, direct injection (e.g., intramuscular injection, intratumoral injection) at the desired treatment site, by introduction of the active agent formulation intravenously at a site near a desired treatment site (e.g., into a vessel or capillary that feeds a treatment site), by intra-arterial introduction, by introduction (e.g., by injection or other method of implantation) of an active agent formulation in a biocompatible gel or capsule within or adjacent a treatment site, by injection directly into muscle or other tissue in which a decrease in pathological angiogenesis is desired, etc.

In another embodiment of interest, the active agent formulation is delivered in the form of a biocompatible gel, which can be implanted (e.g., by injection into or adjacent a treatment site, by extrusion into or adjacent a tissue to be treated, etc.). Gel formulations comprising an active agent can be designed to facilitate local release of the active agent for a sustained period (e.g., over a period of hours, days, weeks, etc.). The gel can be injected into or near a treatment site, e.g., using a needle or other delivery device.

The desirable extent of reduction of pathological angiogenesis will depend on the particular condition or disease being treated, as well as the stability of the patient and possible side-effects.

Screening Assays

The present invention further provides methods of identifying an agent that modulates angiogenesis. The methods generally involve contacting a cell with a test agent, wherein the cell expresses one or more concordantly-regulated angiogenesis-modulating genes; and assessing the effect of the test agent upon expression of the gene. An increase or a decrease in expression of the gene in the presence of the candidate agent relative to a level of expression of the gene in the absence of the test agent indicates the test agent has activity in modulating angiogenic activity, and is a candidate for use in modulating angiogenic activity.

Where a gene expression level affected by a candidate agent is compared to a control level, such as a level of expression of the gene in the absence of the test agent, it is not necessary to conduct such a control in parallel (although the methods provide for optionally conducting such a parallel control assay. Instead, a test gene expression level can be compared to an expected gene expression level under a selected control condition, where the expected gene expression level has been previously determined (e.g., by averaging the results of multiple assays). Thus reference to relative to or compared to "a gene expression level in the absence of the test agent" is not meant to require that such control gene expression level actually be determined in a parallel as part of the recited method.

Suitable cells include endothelial cells, e.g., primary EC, EC cell lines, immortalized EC cells, and the like. Non-limiting examples of suitable EC cells include human umbilical vein endothelial cells (HUVEC); human dermal microvascular endothelial cells (HMVEC); human aortic endothelial cells (HAEC), and the like.

Expression of a concordantly-regulated pro-angiogenic gene and/or concordantly-regulated anti-angiogenic gene can be detected by any suitable means, and may be either qualitative or quantitative. For example, expression can be detected through detection of hybridization of RNA from a sample (or cDNA generated from such RNA) to nucleic acid of the genes to be assayed, as exemplified below, through use of nucleic amplification techniques, or other nucleic acid-based detection methods. Other methods for detecting gene expression include, but are not necessarily limited to use, use of recombinant reporter constructs, which constructs provide for production of a detectable signal that is indicative of expression of a concordantly-regulated angiogenesis-modulating gene in the cell. For example, recombinant cells can be generated having a detectable tag (e.g., a optically detectably polypeptide (e.g., GFP, YFP, and the like)) operably linked to a promoter endogenous to the concordantly-regulated angiogenesis-modulating gene. Detection of the detectable signal associated with the report is then used as a means of assessing concordantly-regulated angiogenesis-modulating gene expression. Where expression multiple concordantly-regulated angiogenesis-modulating genes are assessed from a single cell, different detectable tags which provide for distinguishable detectable signals to facilitate assessment of expression of different genes in the same cell or in different cells in a mixed cell population.

In general, a cell is contacted with a test agent under conditions that would provide for angiogenic modulatory activity of a known angiogenesis modulatory compound (e.g., nAChR agonist or antagonist, bFGF receptor agonist or antagonist, VEGF receptor agonist or antagonist) (e.g., for a suitable period of time (e.g., from about one minute to about 4 hours), and under appropriate culture conditions, etc.). The expression of one or more concordantly-regulated angiogenesis-modulating gene-encoded mRNAs and/or proteins is then detected. In some embodiments, a cell is contacted with a test agent in vitro for a suitable period of time (e.g., from about one minute to about 4 hours); and the level of one or more concordantly-regulated angiogenesis-modulating gene-encoded mRNAs and/or proteins is determined. The presence and/or level of a concordantly-regulated angiogenesis-modulating gene-encoded mRNAs and/or proteins is detected as described above.

The screening methods disclosed herein can be used to identify agents that enhance angiogenesis (e.g., for use in promoting for therapeutic angiogenesis) or inhibit angiogenesis (e.g., for use in inhibiting pathological angiogenesis). The methods generally involve contacting a cell with a test agent, wherein the cell expresses one or more concordantly-regulated angiogenesis-modulating genes; and assessing the effect of the test agent upon expression of the gene(s).

Test agents that increase the expression of 1, 2, 3, 4, 5, 6, 7, 8, 9, 10, or more concordantly-regulated pro-angiogenic genes and/or reduce the expression of 1, 2, 3, 4, 5, 6, 7, 8, 9, 10 or more concordantly-regulated anti-angiogenic genes are identified as agents that increase angiogenesis. Such changes in expression of the gene in the presence of the test agent relative to the level of expression of the gene in the absence of the test agent indicates the test agent has activity in increasing angiogenic activity, and is a candidate for therapeutic angiogenesis.

Similarly the screening methods can be used to identify agents that inhibit angiogenesis (e.g., for use in inhibiting pathological angiogenesis). The methods generally involve contacting a cell with a test agent, wherein the cell expresses one or more concordantly-regulated angiogenesis-modulating genes; and assessing the effect of the test agent upon expression of the gene. Test agents that increase the expression of 1, 2, 3, 4, 5, 6, 7, 8, 9, 10, or more concordantly-regulated anti-angiogenic genes are identified as agents that reduce angiogenesis. Test agents that reduce the expression of 1, 2, 3, 4, 5, 6, 7, 8, 9, 10, or more concordantly-regulated pro-angiogenic genes would also be expected to reduce angiogenesis. Such changes in expression of the gene in the presence of the test agent relative to the level of expression of the gene in the absence of the test agent indicates the test agent has activity in reducing angiogenic activity, and is a candidate for treating pathological neovascularization.

Examples of concordantly-regulated pro-angiogenic genes include RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, and PDE6G. Thus, e.g., where a test agent reduces expression of one or more of RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC 1, or PDE6G. the test agent is likely to reduce angiogenesis. Screening for agents that affect expression of concordantly-regulated pro-angiogenic genes can be accomplished by assessing expression of 1, 2, 3, 4, 5, 6, 7, 8, 9, 10 or more, including all of the above, concordantly-regulated pro-angiogenic genes.

Examples of concordantly-regulated anti-angiogenic genes include TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, and PSME2. Thus, e.g., where a test agent increases expression of one or more of TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2., the test agent is likely to reduce angiogenesis. Screening for agents that affect expression of concordantly-regulated anti-angiogenic genes can be accomplished by assessing expression of 1, 2, 3, 4, 5, 6, 7, 8, 9, 10 or more, including all of the above, concordantly-regulated anti-angiogenic genes. In some embodiments, the concordantly-regulated anti-angiogenic gene is other than TXNIP.

The effect of the test agent in reducing or increasing angiogenesis can be further verified using any of a variety of known assays, e.g., an in vivo Matrigel plug assay; a corneal neovascularization assay; an in vivo/in vitro chick chorioallantoic membrane assay; an in vitro cellular (proliferation, migration, tube formation) assay; and an organotypic (aortic ring) assay.

Expression Profiles in Screening Candidate Agents

The screening methods can also be applied to determine a concordantly-regulated angiogenesis-modulating gene expression profile, which profile is indicative of the candidate agents angiogenic or anti-angiogenic activity. A concordantly-regulated angiogenesis-modulating gene expression profile of a candidate agent can be generated by, for example, contacting a cell with a candidate agent, and assessing the effect of the candidate agent on expression of one or more concordantly-regulated angiogenesis-modulating genes, wherein said assessing provides a concordantly-regulated angiogenesis-modulating gene expression profile.

The concordantly-regulated angiogenesis-modulating gene expression profile elicited in the presence of the candidate agent is indicative of the angiogenic or anti-angiogenic activity of the candidate agent. A concordantly-regulated angiogenesis-modulating gene expression profile in the absence of the candidate agent is normally a negative control. A candidate agent that elicits an angiogenic gene expression profile is one that has having decreased expression of one or more concordantly-regulated anti-angiogenic genes and/or increased expression of one or more concordantly-regulated pro-angiogenic genes in the presence of the candidate agent (e.g., relative to a level of expression of the gene(s) in the absence of the candidate agent), indicating the candidate agent has activity in enhancing angiogenesis. A candidate agent that elicits an anti-angiogenic gene expression profile having increased expression of one or more concordantly-regulated anti-angiogenic genes and/or decreased expression of one or more concordantly-regulated pro-angiogenic genes in the presence of the candidate agent (e.g., relative to a level of expression of the gene(s) in the absence of the candidate agent) indicates the candidate agent has activity in reducing angiogenesis.

The number of genes for which expression is assessed for purposes of generating a gene expression profile can vary. For example, a candidate agent can be classified as having angiogenic activity where it elicits expression profile indicative of up-regulation of 1, 2, 3, 4, 5, 6, 7, 8, 9 10, or more concordantly-regulated pro-angiogenic genes and/or down-regulation of 1, 2, 3, 4, 5, 6, 7, 8, 9, 10 or more concordantly-regulated anti-angiogenic genes. A candidate agent can be classified as having anti-angiogenic activity where it that elicits an expression profile indicative of down-regulation of 1, 2, 3, 4, 5, 6, 7, 8, 9 10, or more concordantly-regulated pro-angiogenic genes and/or up-regulation of 1, 2, 3, 4, 5, 6, 7, 8, 9, 10 or more concordantly-regulated anti-angiogenic genes.

The term "expression profile" is used broadly to include a genomic expression profile, e.g., an expression profile of mRNAs (also referred to as a "transcriptional profile"), or a proteomic expression profile, e.g., an expression profile of one or more different proteins. Profiles may be generated by any convenient means for determining differential gene expression between two samples, e.g. quantitative hybridization of mRNA, labeled mRNA, amplified mRNA, cRNA, etc., quantitative PCR, ELISA for protein quantitation, and the like. The expression profile may include expression data for 5, 10, 20, 25, 30, 35, 40, 45, 50, 55, 60, 65, 70, 75, 80 or more of, including all of the listed concordantly-regulated angiogenesis-modulating genes/proteins which exhibit a statistically significant increase in expression ("up" or "up-regulated") or statistically significant decrease in expression ("down" or "down-regulated") in the presence of a in response to a nAChR agonist (e.g., nicotine), a bFGF receptor agonist (e.g., bFGF), or a VEGF receptor agonist (e.g., VEGF), with the proviso that the therapeutic agent does not mediate a pro-angiogenic effect through direct interaction with a nAChR, bFGF receptor or VEGF receptor (and thus specifically excludes, for example, nicotine, bFGF and VEGF), as disclosed herein.

An "angiogenic expression profile" or "anti-angiogenic expression profile" (also referred to herein as an "angiogenic signature" or "anti-angiogenic signature" respectively) refers to a dataset that provides information on the change in expression of a set of concordantly-regulated angiogenesis-modulating genes that are concordantly regulated in expression following exposure of a cell to a nAChR modulator (e.g., nicotine), a bFGF receptor modulator (e.g., bFGF), and or V EGF receptor modulator (e.g., VEGF), where the cell is exposed to these modulators in separate assays. Of particular interest are the modulators nicotine, bFGF, and VEGF. A useful signature may be obtained from all or a part of a concordantly-regulated angiogenesis-modulating gene dataset, usually the signature will comprise information from at least about 2, 3, 4, 5, 6, 7, 8, 9, 10, 15, 20, 15, 30 or more concordantly-regulated angiogenesis-modulating genes, which genes may including concordantly-regulated pro-angiogenic genes, concordantly-regulated anti-angiogenic genes, or both. Where a subset of a dataset is used, the subset may comprise upregulated genes, downregulated genes, or a combination thereof.

The concordantly-regulated angiogenesis-modulating genes of particular interest in such angiogenic and/or anti-angiogenic gene expression profiles include 1, 2, 3, 4, 5, 6, 7, 8, 9, 10 or more concordantly-regulated anti-angiogenic genes selected from TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, and PSME2 and/or 1, 2, 3, 4, 5, 6, 7, 8, 9, 10 or more concordantly-regulated pro-angiogenic genes selected from RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, and PDE6G. In some embodiments, the concordantly-regulated anti-angiogenic gene is other than TXNIP.

Gene expression profiles can be defined in several ways. For example, a gene expression profile can be the relative transcript level of any number of particular set of genes. Alternatively, a gene expression profile can be defined by comparing the level of expression of a variety of genes in one state to the level of expression of the same genes in another state. For example, genes can be either upregulated, down-regulated, or remain substantially at the same level in both states. Of particular interest in the present disclosure are gene expression profiles indicative expression levels of genes that are up-regulated or down-regulated in the presence of a nAChR modulator (e.g., nAChR agonist or nAChR antagonist (usually a nAChR agonist, e.g., nicotine), a bFGF receptor modulator (e.g., bFGF), and VEGF modulator (e.g., VEGF).

Obtaining a Gene Expression Profile

In certain embodiments, the expression profile obtained is a genomic or nucleic acid expression profile, where the amount or level of one or more nucleic acids in the sample is determined. In these embodiments, the sample that is assayed to generate the expression profile employed in the diagnostic methods is one that is a nucleic acid sample. The nucleic acid sample includes a plurality or population of distinct nucleic acids that includes the expression information of the phenotype determinative genes of interest of the cell or tissue being diagnosed. The nucleic acid may include RNA or DNA nucleic acids, e.g., mRNA, cRNA, cDNA etc., so long as the sample retains the expression information of the host cell or tissue from which it is obtained.

The sample may be prepared in a number of different ways, as is known in the art, e.g., by mRNA isolation from a cell, where the isolated mRNA is used as is, amplified, employed to prepare cDNA, cRNA, etc., as is known in the differential expression art. The sample is typically prepared from a cell or tissue that has been exposed to an agent of interest, and for which a concordantly-regulated angiogenesis-modulating gene expression profile following exposure to a known angiogenesis modulator (e.g., pro- or anti-angiogenic agent), and usually for which a concordantly-regulated angiogenesis-modulating gene expression profile has been determined (e.g., to serve as the basis for control levels of gene expression indicative of an angiogenic and/or anti-angiogenic expression profile).

The expression profile may be generated from the initial nucleic acid sample using any convenient protocol. While a variety of different manners of generating expression profiles are known, such as those employed in the field of differential gene expression analysis, one representative and convenient type of protocol for generating expression profiles is array based gene expression profile generation protocols. Such applications are hybridization assays in which a nucleic acid that displays "probe" nucleic acids for each of the genes to be assayed/profiled in the profile to be generated is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively.

Exemplary hybridization technology which may be practiced to generate the expression profiles employed in the subject methods includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In these methods, an array of "probe" nucleic acids that includes a probe for each of the phenotype determinative genes whose expression is being assayed is contacted with target nucleic acids as described above. Contact is carried out under hybridization conditions, e.g., stringent hybridization conditions as described above, and unbound nucleic acid is then removed. The resultant pattern of hybridized nucleic acid provides information regarding expression for each of the genes that have been probed, where the expression information is in terms of whether or not the gene is expressed and, typically, at what level, where the expression data (expression profile), may be qualitative and/or quantitative.

Alternatively, non-array based methods for quantifying the levels of one or more nucleic acids in a sample may be employed, including quantitative PCR, and the like.

Where the expression profile is a protein expression profile, any convenient protein quantitation protocol may be employed, where the levels of one or more proteins in the assayed sample are determined. Representative methods include, but are not limited to; proteomic arrays, flow cytometry, standard immunoassays, etc.

After obtaining the expression profile from the sample exposed to a candidate agent, the expression profile is compared with a concordantly-regulated angiogenic gene reference profile to determine whether the agent elicits and an angiogenic expression profile, an anti-angiogenic expression profile, or neither. A concordantly-regulated angiogenic gene reference profile is provided, or may be obtained by empirical methods from cells (e.g., endothelial cells) exposed to a known angiogenesis modulators (e.g., known modulators of nAChR and known angiogenic growth factors, particularly VEGF and bFGF). In certain embodiments, the obtained expression profile is compared to a single reference/control profile to obtain information regarding the activity of the candidate agent being tested. In yet other embodiments, the obtained expression profile is compared to two or more different reference/control profiles to obtain additional information regarding the activity of the candidate agent being tested. For example, the obtained expression profile may be compared to a positive and negative reference profile to obtain confirmed information regarding whether the candidate agent has an angiogenic or anti-angiogenic effect.

The difference values (i.e. values indicative of a difference in expression in the presence of an agent compared to in the absence of an agent) may be performed using any convenient methodology, where a variety of methodologies are known to those of skill in the array art, e.g., by comparing digital images of the expression profiles, by comparing databases of expression data, etc. Patents describing ways of comparing expression profiles include, but are not limited to, U.S. Pat. Nos. 6,308,170 and 6,228,575, the disclosures of which are herein incorporated by reference.

Classification of a candidate agent as having an angiogenic or anti-angiogenic activity can be probabilistically defined, where the cut-off may be empirically derived. For example, a probability of about 0.4, more usually a probability of about 0.5, or a probability of about 0.6 or higher may be used to distinguish between candidate agents that have or lack an angiogenic or anti-angiogenic activity as determined by concordantly-regulated angiogenesis-modulating gene expression analysis. A "high" probability may be at least about 0.75, at least about 0.7, at least about 0.6, or at least about 0.5. A "low" probability may be not more than about 0.25, not more than 0.3, or not more than 0.4. In many embodiments, the above-obtained information about the candidate agent being assayed is employed to predict whether a candidate agent will have angiogenic or anti-angiogenic activity in vivo. The assays can also be used to determine likely dose-response in vivo, and thus can provide information for dose optimization.

Statistical Analysis

Various methods for statistical analysis of concordantly-regulated angiogenesis-modulating gene expression profile data can be applied to determine whether a pattern of concordantly-regulated angiogenesis-modulating gene expression in the presence of a candidate agent indicates the agent has activity as a pro-angiogenic agent or an anti-angiogenic agent. For example, hierarchical clustering can be used to assess the similarity between the CSR signature and a test gene expression, by setting an arbitrary threshold for assigning a candidate agent to one of two groups (e.g., providing for increased expression of a concordantly-regulated angiogenesis-modulating gene ("up") or providing for decreased expression of a concordantly-regulated angiogenesis-modulating gene ("down").

Alternatively, in a the threshold for assignment is treated as a parameter, which can be used to quantify the confidence with which a candidate agent has activity as a pro- or anti-angiogenic agent. The threshold for assignment can be scaled to favor sensitivity or specificity, depending on the clinical scenario. In one such method, the concordantly-regulated angiogenesis-modulating gene expression profile in a test candidate agent sample is correlated to a vector representing the centroid of the differential expression of a reference concordantly-regulated angiogenesis-modulating gene expression signature (e.g., a concordantly-regulated pro-angiogenic gene expression signature or a concordantly-regulated anti-angiogenic gene expression signature).

For example, expression data can be subjected to transformation and normalization. For example, ratios are generated by mean centering the expression data for each gene (by dividing the intensity measurement for each gene on a given array by the average intensity of the gene across all arrays), (2) then log-transformed (base 2) the resulting ratios, and (3) then median centered the expression data across arrays then across genes.

Where gene expression is assessed using cDNA microarray data, genes with hybridization signals at least about 2.5-fold greater than the local background fluorescent signal in the reference channel are considered adequately measured. The genes are centered by mean value within each dataset, and average linkage clustering carried out.

Gene expression levels resulting from contacting a cell with an agent are segregated into two classes based on the first bifurcation in the hierarchical clustering "dendrogram". The expected changes in expression of concordantly-regulated angiogenesis-modulating genes in the expression data allows for classifying a candidate agent as a pro-angiogenic or anti-angiogenic agent. For example, candidate agents that result in generally high levels of expression of concordantly-regulated pro-angiogenic genes and low levels of expression of the concordantly-regulated anti-angiogenic genes, are classified as pro-angiogenic agents. Conversely, candidate agents that result in generally high levels of expression of concordantly-regulated anti-angiogenic gene and low levels of expression of the concordantly-regulated pro-angiogenic genes, are classified as anti-angiogenic agents.

A Pearson correlation of the averaged concordantly-regulated angiogenesis-modulating gene expression pattern with the gene expression from the candidate agent-stimulated cell sample can be calculated. The Pearson correlation data can facilitate determining whether the candidate agent elicits a gene expression profile that is positively correlated to a concordantly-regulated angiogenesis-modulating gene expression pattern, e.g., as being positively correlated with a pro-angiogenic gene expression pattern or as being positively correlated with an anti-angiogenic gene expression pattern. The Pearson correlation should be statistically significant, e.g., a probability of about 0.4, more usually a probability of about 0.5, or a probability of about 0.6 or higher may be used to distinguish between candidate agents that have or lack an angiogenic or anti-angiogenic activity as determined by concordantly-regulated angiogenesis-modulating gene expression analysis. A "high" probability may be at least about 0.75, at least about 0.7, at least about 0.6, or at least about 0.5. A "low" probability may be not more than about 0.25, not more than 0.3, or not more than 0.4.

To address the level of redundancy of concordantly-regulated angiogenesis-modulating genes in classifying a candidate agent as pro-angiogenic or anti-angiogenic (or as having no significant pro-angiogenic or anti-angiogenic effect), a shrunken centroid analysis can be applied, using Prediction Analysis of Microarrays (PAM).

In a preferred method, the techniques employed are similar to those disclosed in Chang H Y. PLoS Biol. 2004; 2: e7), which involve firstly defining a gene expression profile that predicts a phenotype (e.g. pro- or anti-angiogenesis), often with the aid of an organizing and visualizing tool such as hierarchical clustering (as used in the Examples provided herein). A profile elicited by a candidate agent is compared to a known pro- and/or anti-angiogenic profile to identify a "matching" profile, where the comparison can be conducted using a variety of pattern recognition techniques such as clustering.

"Matching profile" as used herein includes but does not require an exact match, where an increase in the similarity of a candidate agent expression profile and an expression profile of a known pro- or anti-angiogenic agent (e.g., a known nAChR agonist or nAChR antagonist) provides for increased confidence that the candidate agent has the activity of the agent that generated the reference profile. For example, the more concordantly-regulated pro-angiogenic genes that are increased in expression in the presence of a candidate agent (e.g., 2 or more, 3 or more, 4 or more, 5 or more, 6 or more, 7 or more, 8 or more, 9 or more, or 10 or more concordantly-regulated pro-angiogenic genes) and/or the more concordantly-regulated anti-angiogenic genes that are decreased in expression in the presence of the candidate agent (e.g., 2 or more, 3 or more, 4 or more, 5 or more, 6 or more, 7 or more, 8 or more, 9 or more, or 10 or more concordantly-regulated anti-angiogenic genes), or a combination thereof (e.g., 1, 2 or more concordantly-regulated pro-angiogenic genes increased in expression, and 1, 2 or more concordantly-regulated anti-angiogenic genes decreased in expression), the greater the confidence the candidate agent mimics activity of a known angiogenic agent (e.g., a nAChR agonist).

Similarly, the more concordantly-regulated anti-angiogenic genes that are increased in expression in the presence of a candidate agent (e.g., 2 or more, 3 or more, 4 or more, 5 or more, 6 or more, 7 or more, 8 or more, 9 or more, or 10 or more concordantly-regulated anti-angiogenic genes) and/or the more concordantly-regulated pro-angiogenic genes that are decreased in expression in the presence of the candidate agent (e.g., 2 or more, 3 or more, 4 or more, 5 or more, 6 or more, 7 or more, 8 or more, 9 or more, or 10 or more concordantly-regulated pro-angiogenic genes), or a combination thereof (e.g., 1, 2 or more concordantly-regulated anti-angiogenic genes increased in expression, and 1, 2 or concordantly-regulated pro-angiogenic genes decreased in expression), the greater the confidence the candidate agent mimics activity of a known anti-angiogenic agent.

Criteria for significant up- or down-regulation can be based on identifying genes which have undergone statistically significant changes in gene expression using Significance Analysis of Microarrays (SAM; Tusher, V G. PNAS, 2001; 98:5116, incorporated by reference herein). SAM uses permutations of repeated measurements to estimate the percentage of genes identified by chance, termed the false discovery rate (FDR).

In one approach to significance ordering, the FDR can be determined by first generating a set of null distributions of dissimilarity values is generated. In one example, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). The set of null distribution is obtained by: permuting the values of each profile for all available profiles; calculating the pairwise correlation coefficients for all profile; calculating the probability density function of the correlation coefficients for this permutation; and repeating the procedure for N times. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value may be applied to the correlations between experimental profiles.

Using the distribution above, a level of confidence is chosen for significance. This is used to determine the lowest value of the correlation coefficient that exceeds the result that would have obtained by chance. Using this method, a threshold is obtained for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation.

The data may be subjected to non-supervised hierarchical clustering to reveal relationships among profiles. For example, hierarchical clustering may be performed, where the Pearson correlation is employed as the clustering metric. Clustering of the correlation matrix, e.g. using multidimensional scaling, enhances the visualization of functional homology similarities and dissimilarities. Multidimensional scaling (MDS) can be applied in one, two or three dimensions.

For the data provided in Tables 1 and 2 in the Examples below, significant up- or down-regulation was based on identification by SAM analysis where the FDR was set at less than or equal to 5%, with no fold change in expression cut-off criteria. For each significantly changed gene, a Q value was generated by SAM analysis, where the Q value indicates the likelihood that the finding with regards to that gene is false.

Implementation of Gene Expression Analysis

Analysis of gene expression may be implemented in hardware or software, or a combination of both. For example, a machine-readable storage medium can be provided, the medium comprising a data storage material encoded with machine readable data which, when using a machine programmed with instructions for using said data, is capable of displaying a any of the datasets and data comparisons. The methods disclosed herein can be implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer may be, for example, a personal computer, microcomputer, or workstation of conventional design.

Each program are usually be implemented in a high level procedural or object oriented programming language to communicate with a computer system. However, the programs can also be implemented in assembly or machine language, if desired. In any case, the language may be a compiled or interpreted language. Each such computer program is preferably stored on a storage media or device (e.g., ROM or magnetic diskette) readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems described herein. One format for an output means test datasets possessing varying degrees of similarity to a trusted profile. Such presentation provides a skilled artisan with a ranking of similarities and identifies the degree of similarity contained in the test pattern.

The concordantly-regulated angiogenesis-modulating gene expression data can include the data set out herein (see, e.g., Tables 1 and 2 in the Examples).

Databases of Concordantly-Regulated Angiogenesis-modulating Gene Expression Profiles Also provided are databases of expression profiles of concordantly-regulated angiogenesis-modulating genes. Such databases will typically comprise expression profiles derived from contacting suitable cells, usually endothelial cells, with a known pro-angiogenic agent (e.g., a known nAChR agonist, a known bFGF receptor agonist, or known VEGF receptor agonist) or known anti-angiogenic agent (e.g., a nAChR antagonist, a known bFGF receptor antagonist, or known VEGF receptor antagonist).

The expression profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

Agents for Screening

In the context of screening assays disclosed herein, the terms "agent", "substance", and "compound" are used interchangeably herein, as are the terms "candidate agent," and "test agent", to refer to agents used in screening assays to identify those having a desired activity in modulating angiogenesis according to the present invention. "Agents" encompass numerous biological and chemical classes, including synthetic, semi-synthetic, or naturally-occurring inorganic or organic molecules, including synthetic, recombinant or naturally-occurring polypeptides and nucleic acids (e.g., nucleic acids encoding a gene product, antisense RNA, siRNA, and the like). Salts, particularly pharmaceutically acceptable salts, of the foregoing are also encompassed within the meaning of agent. "Candidate agents" or "test agents" particularly include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

In general, agents of interest include small organic or inorganic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The agents may comprise cyclical carbon or heterocyclic structures and/or aromatic or polyaromatic structures substituted with one or more of the above functional groups. Agents, particularly candidate agents, are also found among biomolecules including peptides, saccharides, fatty acids, steroids, purines, pyrimidines, derivatives, structural analogs, salts thereof or combinations of the foregoing.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The components of the assay mixture are added in any order that provides for the requisite binding or other activity. Incubations are performed at any suitable temperature, typically between 4° C. and 40° C. Incubation periods are selected for optimum activity, but may also be optimized to facilitate rapid high-throughput screening. Typically between 0.1 and 1 hour will be sufficient.

Nucleic Acid Arrays

A subject nucleic acid array comprises an array of probe nucleic acids immobilized on a solid support surface. A subject array will generally comprise a support with at least one surface and a plurality of different polynucleotide probes. Each different polynucleotide probe hybridizes under stringent hybridization conditions to a gene product of a concordantly-regulated angiogenesis-modulating gene.

In some embodiments, a subject array comprises oligonucleotide probes that hybridize under stringent hybridization conditions with one or more of TXNIP, CCL2, CCL7, CCL8, CCL20, CX3CL, TNFRSF1B, EP300, CD53, SQSTM1, ICAM1, EPHB4, EPHA2, MT1E, MT1F, MT1G, MT1L, MT1X, TM2A, MT3, MYC, ERCC2, PTLP, CACNA1D, COTL1, ZNF200, RPS9, RPL29, RPL27A, RPL10, PFKP, MT2A, MT1L, MT1F, FLJ33706, FLJ12442, FARSLA, CACNA1D, EP300, TAGLN, TIMM8B, PLK2, or PSME2.

In some embodiments, a subject array comprises oligonucleotide probes that hybridize under stringent hybridization conditions with one or more RIN2, ERBB2IP, ADAM9, RRM2, MDM2, AHR, MLLT4, MUTYH, BCL10, CASP8AP2, LOX, ASPH, ARHGAP5, ARHGAP21, ATHGAP24, ARHGEF7, Cdc42, Rac, PAK1, ZNF561, SOX17, SMC4L1, SLC7A2, PRAC, PCYOX1, P4HA1, LOC87769, K5B, FLJ12847, CR1L, A2M, GAB1, SOCS6, C20orf140, CR1L, PANK3, SENP2, PEG10, RDH13, TSN, BBOX1, PAICS, MKI67, RB1CC1, or PDE6G.

Nucleic acid probes are generally oligonucleotides, e.g. oligonucleotides of at least about 12 nucleotides (nt), at least about 15 nt, at least about 18 nt, at least about 20 nt, at least about 25 nt, at least about 30 nt, at least about 40 nt, at least about 50 at least about, at least about 60 nt, or longer.

A variety of different array formats are known in the art, with a wide variety of different probe structures, substrate compositions and attachment technologies. Representative array structures of interest include those described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

A number of methods are available for creating microarrays of nucleic acids to be used in DNA hybridization assays. Exemplary are PCT application Ser. No. W95/35505, published Dec. 28, 1995; U.S. Pat. No. 5,445,934, issued, Aug. 29, 1995; and Drmanac et al. (1993) *Science* 260:1649-1652. Yershov et al. (1996) *Genetics* 93:4913-4918 describe an alternative construction of an oligonucleotide array. The construction and use of oligonucleotide arrays is reviewed by Ramsay (1998) supra. Methods of using high density oligonucleotide arrays are known in the art. For example, Milosavljevic et al. (1996) *Genomics* 37:77-86 describe DNA sequence recognition by hybridization to short oligomers.

The systems and kits of the subject invention may include the above-described arrays. The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

Any convenient protocol for assaying a sample for the presence of a nucleic acid that hybridizes with a nucleic acid in a subject array may be employed in the subject methods. For example, a polynucleotide sample derived from (e.g., obtained from) an individual is employed. Any biological sample that comprises a polynucleotide from the individual is suitable for use in the methods of the invention. The biological sample may be processed so as to isolate the polynucleotide. Alternatively, whole cells or other biological samples may be used without isolation of the polynucleotides contained therein. A test nucleic acid sample can be amplified with primers which amplify a region known to comprise the target nucleic acid. Genomic DNA or mRNA can be used directly. The target nucleic acid may be amplified by conventional techniques, such as a polymerase chain reaction (PCR), to provide sufficient amounts for analysis. The use of the polymerase chain reaction is described in a variety of publications, including, e.g., "PCR Protocols (Methods in Molecular Biology)" (2000) J. M. S. Bartlett and D. Stirling, eds, Humana Press; and "PCR Applications: Protocols for Functional Genomics" (1999) Innis, Gelfand, and Sninsky, eds., Academic Press.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Detection of hybridization between a nucleic acid in a subject array and a nucleic acid in the biological sample derived from an individual can be accomplished by any means known in the art. Hybridization analysis can be carried out in a number of different ways, including, but not limited to Southern blots, Northern blots, dot blots, microarrays, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Detection of a hybridizing nucleic acid in a nucleic acid sample can be performed by hybridizing a sample and control nucleic acids to a subject nucleic acid array. Cronin et al. (1996) *Human Mutation* 7:244-255; and Kozal et al. (1996) *Nature Med.* 2:753-759.

In some embodiments, a subject method is a hybridization assay in which a subject nucleic acid array that displays "probe" nucleic acids for target nucleic acids to be assayed/profiled is employed. In these assays, a sample of target nucleic acids is first prepared from the initial nucleic acid sample being assayed, where preparation may include labeling of the target nucleic acids with a label, e.g., a member of signal producing system. Following target nucleic acid sample preparation, the sample is contacted with the array under hybridization conditions, whereby complexes are formed between target nucleic acids that are complementary to probe sequences attached to the array surface. The presence of hybridized complexes is then detected, either qualitatively or quantitatively. Specific hybridization technology which may be practiced to generate the information (e.g., information regarding the presence of (or absence from) hybridizing nucleic acid in a sample) includes the technology described in U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. Contact between a probe and a target nucleic acid is carried out under hybridization conditions, e.g., stringent hybridization conditions, and unbound nucleic acid is then removed.

Reagents and Kits

The present disclosure also provides reagents and kits thereof for practicing one or more of the above-described methods. The subject reagents and kits thereof may vary greatly. For example, reagents of interest include reagents specifically designed for use in production of the above described concordantly-regulated angiogenesis-modulating gene expression profiles of determinative genes, such as the concordantly-regulated pro-angiogenic and concordantly-regulated anti-angiogenic genes disclosed herein.

One type of such reagent is an array of probe nucleic acids in which concordantly-regulated angiogenesis-modulating genes of interest are represented, such as those exemplified in the disclosure above. As discussed above, a variety of different array formats are known in the art, with a wide variety of different probe structures, substrate compositions and attachment technologies. Representative array structures of interest include those described in U.S. Pat. Nos. 5,143,854; 5,288, 644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280. In certain embodiments, the number of genes that are from that is represented on the array is at least 5, 10, 15, 20, or 25, and may be at least 50 or up to including all of the concordantly-regulated angiogenesis-modulating genes disclosed herein. Optionally, probes for control genes (e.g., housekeeping genes) or other genes may be included on the array.

Another type of reagent that is specifically tailored for generating expression profiles of concordantly-regulated angiogenesis-modulating genes is a collection of gene specific primers that is designed to selectively amplify such genes, for use in quantitative PCR and other quantitation methods. Gene specific primers and methods for using the same are described in U.S. Pat. No. 5,994,076, the disclosure of which is herein incorporated by reference. Of particular interest are collections of gene specific primers that have primers for at least 5, 10, 15, 20, or 25, and may be at least 50 or up to including all of the concordantly-regulated angiogenesis-modulating genes disclosed herein. The subject gene specific primer collections may include only concordantly-regulated angiogenesis-modulating genes, or only concordantly-regulated pro-angiogenic genes or only concordantly-regulated anti-angiogenic genes. Optionally, primers for control genes (e.g., housekeeping genes) or other genes may be included.

The kits may include the above described arrays and/or gene specific primer collections. The kits may further include a software package for statistical analysis of one or more phenotypes, and may include a reference database for calculating the probability a candidate agent has a desired activity in modulating angiogenesis. The reference dataset can be a reference dataset for at least one of a nAChR modulator (e.g., nAChR agonist (e.g., nicotine) or nAChR antagonist), a bFGF receptor modulator (e.g., bFGF agonist (e.g., bFGF) or antagonist), and or VEGF receptor modulator (e.g., VEGF receptor agonist (e.g., VEGF) or antagonist), and can include multiple different agonists and/or antagonists of these receptors. The kit may include reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The above-described analytical methods may be embodied as a program of instructions executable by computer to perform the different aspects of the invention. Any of the techniques described above may be performed by means of software components loaded into a computer or other information appliance or digital device. When so enabled, the computer, appliance or device may then perform the above-described techniques to assist the analysis of sets of values associated with a plurality of genes in the manner described above, or for comparing such associated values. The software component may be loaded from a fixed media or accessed through a communication medium such as the internet or other type of computer network. The above features are embodied in one or more computer programs may be performed by one or more computers running such programs.

Active Agents, Dosages, Formulations, Routes of Administration

Upon reading the present specification, the ordinarily skilled artisan will appreciate that the pharmaceutical compositions comprising an active agent (e.g., an active agent that stimulates expression of one or more concordantly-regulated pro-angiogenic genes, for use in stimulating angiogenesis; an active agent that reduces expression of one or more concordantly-regulated pro-angiogenic genes, for use in reducing pathological angiogenesis) described herein can be provided in a wide variety of formulations. More particularly, the active agent can be formulated into pharmaceutical compositions by combination with appropriate, pharmaceutically acceptable carriers or diluents, and may be formulated into preparations in solid, semi-solid (e.g., gel), liquid or gaseous forms, such as tablets, capsules, powders, granules, ointments, solutions, suppositories, injections, inhalants and aerosols. Where the active agent is a naturally-occurring compound, the pharmaceutical composition can also be provided as an herbal preparation (e.g., as a poultice of plant matter, in a botanical preparation, etc.).

A formulation comprising an active agent will vary according to the condition or disease to be treated, the route of administration, the amount of active agent to be administered, and other variables that will be readily appreciated by the ordinarily skilled artisan. In general, and as discussed in more detail below, administration of an active agent can be either systemic or local, and can be achieved in various ways, including, but not necessarily limited to, administration by a route that is parenteral, intravenous, intratumoral, peritumoral, intra-arterial, inter-pericardial, intramuscular, intraperitoneal, transdermal, transcutaneous, subdermal, intradermal, subcutaneous, intrapulmonary, etc.

In pharmaceutical dosage forms, the active agent may be administered in the form of their pharmaceutically acceptable salts, or they may also be used alone or in appropriate association, as well as in combination, with other pharmaceutically active compounds. The following methods and excipients are merely exemplary and are in no way limiting.

The active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Formulations suitable for topical, transcutaneous, and transdermal administration, e.g., to administer the active agent directly to a wound, may be similarly prepared through use of appropriate suspending agents, solubilizers, thickening agents, stabilizers, and preservatives. Topical formulations may be also utilized with a means to provide continuous administration of an active agent by, for example, incorporation into slow-release pellets or controlled-release patches.

The active agent can also be formulated in a biocompatible gel, which gel can be applied topically (e.g., to facilitate wound healing) or implanted (e.g., to provide for sustained release of active agent at an internal treatment site). Suitable gels and methods for formulating a desired compound for delivery using the gel are well known in the art (see, e.g., U.S. Pat. Nos. 5,801,033; 5,827,937; 5,700,848; and MATRIGEL™).

For oral preparations, the active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The active agent can be utilized in aerosol formulation to be administered via inhalation. The compounds of the present invention can be formulated into pressurized acceptable propellants such as dichlorodifluoromethane, propane, nitrogen and the like.

Furthermore, the active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and/or animal subjects, each unit containing a predetermined quantity of active agent calculated in an amount sufficient to produce the desired angiogenic and/or vasculogenic effect in association with a pharmaceutically acceptable diluent, carrier or vehicle. The specifications for the unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public Particularly where the active agent is to be delivered for local application, e.g., by an intramuscular route, it may be desirable to provide the active agent in a gel or matrix that can support angiogenesis, e.g., migration and proliferation of vascular cells into the matrix with endothelial tube formation. The gel or matrix can thus provide at least the initial substrate upon which new vessels form. For example, the gel or matrix can be extruded into an ischemic region to form a path for new blood vessel formation so as to bypass an obstruction in the area.

The dose of an active agent administered to a subject, particularly a human, in the context of the present invention should be sufficient to effect angiogenesis in a therapeutic manner in the subject over a reasonable time frame. The dose will be determined by the potency of the particular active agent employed and the condition of the subject, as well as the body weight of the subject to be treated. For example, the level or affinity or both of the active agent for the nicotinic acetylcholine receptor may play a role in regulating the compound's effect on angiogenesis. The size of the dose also will be determined by the existence, nature, and extent of any adverse side-effects that might accompany the administration of a particular compound.

In determining the effective amount of active agent in the stimulation of angiogenesis, the route of administration, the kinetics of the release system (e.g., pill, gel or other matrix), and the potency of the active agent is considered so as to achieve the desired angiogenic or anti-angiogenic effect with minimal adverse side effects. The active agent will typically be administered to the subject being treated for a time period ranging from a day to a few weeks, consistent with the clinical condition of the treated subject.

As will be readily apparent to the ordinarily skilled artisan, the dosage is adjusted for various active agents according to their potency and/or efficacy relative to nicotine. If given orally or as an inhalant, the dose may be in the range of about 0.01 mg to 10 mg, given 1 to 20 times daily, and can be up to a total daily dose of about 0.1 mg to 100 mg. If applied topically, for the purpose of a systemic effect, the patch or cream would be designed to provide for systemic delivery of a dose in the range of about 0.01 mg to 10 mg. If the purpose of the topical formulation (e.g., cream) is to provide a local angiogenic effect, the dose would likely be in the range of about 0.001 mg to 1 mg. If injected for the purpose of a systemic effect, the matrix in which the active agent is administered is designed to provide for a systemic delivery of a dose in the range of about 0.001 mg to 1 mg. If injected for the purpose of a local effect, the matrix is designed to release locally an amount of active agent in the range of about 0.003 mg to 1 mg.

Regardless of the route of administration, the dose of active agent can be administered over any appropriate time period, e.g., over the course of 1 to 24 hours, over one to several days, etc. Furthermore, multiple doses can be administered over a selected time period. A suitable dose can be administered in suitable subdoses per day, particularly in a prophylactic regimen. The precise treatment level will be dependent upon the response of the subject being treated.

Of particular interest are agents that a siNAs, as described above. Exemplary formulations and methods for the delivery of nucleic acid molecules are known in the art. For example, nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see, e.g., Gonzalez et al., 1999, *Bioconjugate Chem.* 10:1068-74; WO 03/47518 and WO 03/46185), poly(lactic-co-glycolic)acid (PLGA) and PLCA microspheres (see, e.g., U.S. Pat. No. 6,447,796 and US 2002/130430), biodegradable nanocapsules, and bioadhesive microspheres, or by proteinaceous vectors (WO 00/53722). In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. In one embodiment, the nucleic acid molecules of the invention are formulated as described in US 2003/0077829, incorporated by reference herein in its entirety.

In one embodiment, a siNA molecule is complexed with membrane disruptive agents such as those described in US 2001/0007666, incorporated by reference herein in its entirety. In another embodiment, the membrane disruptive agent or agents and the siNA molecule are also complexed with a cationic lipid or helper lipid molecule, such as those lipids described in U.S. Pat. No. 6,235,310, incorporated by reference herein in its entirety. In one embodiment, a siNA molecule is complexed with delivery systems as described in US 2003/077829, WO 00/03683 and WO 02/087541, each incorporated herein by reference.

Alternatively, certain siNA molecules of the instant invention can be expressed within cells from eukaryotic promoters (e.g., Izant et al., 1985, *Science* 229:345; McGarry et al., 1986, *Proc. Natl. Acad. Sci. USA* 83:399; Scanlon et al., 1991, *Proc. Natl. Acad Sci. USA* 88:10591-5; Kashani-Sabet et al., 1992, *Antisense Res. Dev.* 2:3-15; Dropulic et al., 1992, *J. Virol.* 66:1432-41; Weerasinghe et al., 1991, *J. Virol.* 65: 5531-4; Ojwang et al., 1992, *Proc. Natl. Acad. Sci. USA* 89:10802-6; Chen et al., 1992, *Nucleic Acids Res.* 20:4581-9; Sarver et al., 1990 Science 247:1222-5; Thompson et al., 1995, *Nucleic Acids Res.* 23:2259; Good et al., 1997, *Gene Therapy* 4:45. Those skilled in the art realize that any nucleic acid can be expressed in eukaryotic cells from the appropriate DNA/RNA vector. The activity of such nucleic acids can be augmented by their release from the primary transcript by an enzymatic nucleic acid (WO 93/23569; WO 94/02595; Ohkawa et al., 1992, *Nucleic Acids Symp. Ser.* 27:15-6; Taira et al., 1991, *NucleicAcids Res.* 19:5125-30; Ventura et al., 1993, Nucleic Acids Res. 21:3249-55; Chowrira et al., 1994, *J. Biol. Chem.* 269:25856.

Where the siNA is an RNA molecule, the siNA can be expressed from transcription units inserted into a vector. The recombinant vectors can be DNA plasmids, non-viral vectors or viral vectors. siNA expressing viral vectors can be constructed based on, but not limited to, adeno-associated virus, retrovirus, adenovirus, or alphavirus. The recombinant vectors capable of expressing the siNA molecules can be delivered as described above, and provide for transient or stable expression. For example, such vectors can include: 1) a transcription initiation region; 2) optionally, a transcription termination region; and 3) a nucleic acid sequence encoding at least one strand of an siNA molecule, wherein the sequence is operably linked to the initiation region and the termination region in a manner that allows expression and/or delivery of the siNA molecule.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Methods and Materials

The following materials and methods are used in the Examples below.

Materials and Reagents. All cells and growth media were purchased from Cambrex-BioSciences (Walkersville, Md.). Nicotine (free base), hexamethonium bromide, mecamylamine and α-bungarotoxin were purchased from Sigma-Aldrich (St. Louis, Mo.). Human VEGF165 and human bFGF were purchased from R&D Systems Inc (Minneapolis, Minn.). All cDNA microarray slides were obtained from the Stanford Functional Genomics Facility (SFGF, Stanford, Calif.), and all microarray reagents were from Invitrogen (Carlsbad, Calif.), Stratagene (La Jolla, Calif.) or Amersham Biosciences (Piscataway, N.J.).

Cell Culture. Adult dermal microvascular cells (HMVEC) were purchased from Cambrex-BioSciences (Walkersville, Md.) as frozen aliquots at passage 3. The cells were expanded and used for both cell culture and microarray investigations at no later than passage seven. Cells were grown under standard conditions of 37° C. in a 95% $O_2$/5% $CO_2$ atmosphere in EBM-MV2 media using 5% Fetal Bovine Serum (FBS) with supplements and antibiotics as per manufacturer's protocol.

Cell Migration Assay. We employed the cell migration assay (9) on early passage (P<7) HMVEC. Control conditions were 1% FBS/EBM. Angiogenic factors or vehicle were added in the following concentrations: nicotine ($10^{-8}$M to $10^{-4}$M), VEGF (1-10 ng/ml), or bFGF (1-10 ng/ml). In some cases, antagonists of the nAChR were co-administered including hexamethonium bromide (10−8M to $10^{-4}$M), mecamylamine ($10^{-8}$M to $10^{-4}$M), or α-bungarotoxin (10 ng/ml). The extent of migration was quantified by counting the number of cells mobilized into the denuded area for a total of twelve microscopic fields of view (125×) per 60 mm plate (Leitz Labovert FS visible light microscope; Leitz, Wetzlar, Germany). All cell biology assays were performed by individuals blinded to treatments and repeated using at least two independent vials of primary cells, with each experiment reproduced three separate times, and each condition within an experiment performed in triplicate.

Microarray Analyses. HMVECs were grown to 50-70% confluency. Subconfluent rather than confluent HMVEC cultures were studied because they more closely resemble conditions associated with cell migration in vivo, and because this condition is associated with increased EC expression of α7-nAChRs. Heeschen et al. (2002) *J. Clin. Invest.* 110:527-536. The concentration of the FBS in the media was then reduced to 1% so as to render the endothelial cells quiescent. After 24 hours, nicotine ($10^{-8}$M), VEGF (10 ng/ml) or bFGF (10 ng/ml) was added. Total RNA was then harvested at 24 hours. Five separate experiments per condition were processed for cDNA microarray analysis. Fluorescently labeled cDNAs (stimulated HMVECs versus vehicle-treated HMVECs at 24 hours post incubation) were hybridized on cDNA microarrays containing 39711 nonredundant cDNA clones, representing 26,260 unique UniGene clusters (SFGF, Stanford, Calif.). Eisen et al. (1998) *Proc Natl Acad Sci USA* 95:14863-14868. Scanning of processed microarray slides was performed using a GenePix400A scanner and images analysed with GENEPIX PRO software (Axon Instruments, Foster City, Calif.). Microarray data were stored in the Stanford Microarray Database (Stanford, Calif.). Spots with signal less than 2.5-fold above background were removed in both channels and/or a regression correlation of less than 0.6. Genes with less than 80% evaluable data were excluded and the remaining data was then normalized. The significance of microarrays (SAM) algorithm was used with a one-class design to identify genes differentially expressed by treatment with each stimuli at each timepoint. Tusher et al. (2001) *Proc Natl Acad Sci USA.* 98:5116-5121. Delta values giving approximately 5% false discovery were chosen. To analyze convergent gene expression profiles, all differentially expressed genes at 24 hours were hierarchically clustered by gene and by array (Cluster software, version 2.11), and the results analysed with Treeview software (version 1.6). Eisen et al. (1998) supra.

Statistical Analysis. Measurement of all thioredoxin and migration activity assays revealed Gaussian distribution. Hence, comparisons between groups were analyzed by t-test (two-sided) or ANOVA for experiments with more than two groups. Post-hoc range tests and pairwise multiple comparisons were performed with the t-tests (two-sided) with Bonferonni correction.

Real-time RT-PCR analysis of Thioredoxin Interacting Protein (TXNIP). Primer and fluorogenic probe sets for TXNIP and GAPDH were designed using Primer Express V2.0 software (Applied Biosystems, Foster City, Calif.). The TXNIP forward and reverse primers and fluorescent-labeled probes were 5'-AGATCAGGTCTAAGCAGCAGAACA-3' (SEQ ID NO: 1), 5'-TCAGATCTACCCAACTCATCT-CAGA-3' (SEQ ID NO:2), and 5'-CCAGCATGGCCAGC-CGAACC-3' (SEQ ID NO:3), respectively. The 5' fluorogenic reporter probe was 6-carboxy-fluorescein (FAM), and 3' fluorogenic quencher was 6-carboxytetramethyl-rhodamine (TAMRA). Primers and probes were synthesized by the Peptide and Nucleic Acid (PAN) Facility at Stanford University. cDNA was synthesized and amplified from 10 ng of total RNA using TaqMan One-Step RT-PCR master Mix Reagents Kit (Applied Biosystems). Amplification was performed on ABI Prism 7900HT Sequence Detection System. All samples were in triplicate. The reaction conditions were at 48° C. for 30 minutes and at 95° C. for 10 minutes followed by 40 cycles of 95° C. for 15 seconds and 60° C. for 1 minute. Reactions without template and/or enzyme were used as negative controls. GAPDH was used as an internal control. RNA quantity was expressed relative to the corresponding GAPDH control. Fold induction over control is determined by normalizing treated samples to the control.

Thioredoxin Bioassay. Thioredoxin was assayed based upon previously published colorimetric protocols. Wang et al. (2002) *J. Biol Chem.* 277:26496-26500. The level of thioredoxin activity is assessed at 412 rim via the oxidation of a colorimetric substrate DTNB (5,5'-dithiobis(2-nitrobenzoic acid)). Protein extracts were obtained by subjecting cells to a lysis buffer (20 mM HEPES (pH 7.9), 300 mM NaCl, 100 mM KCl, 10 mM EDTA, 0.1% Nonidet P-40, PMSF protease inhibitors).

siRNAs. Double-stranded siRNA were designed using siRNA Target Find™ software from Ambion. Each siRNA was optimized for its G/C content, sequence constraints and BLAST search. The knockdown of siRNA was confirmed by mRNA examination. The target sequence, sense siRNA and antisense siRNA for ARHGEF7, Rin2, P4HA1 and TXNIP are provided in the table below. Lower case letters indicate dideoxynucleotides.

```
ARHGEF7:
Target sequence:
5'--  AAGCCTGTGTCTCCCAAATCA -3'    (SEQ ID NO: 4)

Sense siRNA:
5'--  GCCUGUGUCUCCCAAAUCAtt -3'    (SEQ ID NO: 5)

Antisense siRNA:
5'--- UGAUUUGGGAGACACAGGCtt -3'    (SEQ ID NO: 6)

Rin2:
Target sequence:
5'- AACTGAAACAGGAGATGGTGC -3'      (SEQ ID NO: 7)

Sense siRNA:
5'- CUGAAACAGGAGAUGGUGCtt -3'      (SEQ ID NO: 8)

Antisense siRNA:
5'- GCACCAUCUCCUGUUUCAGtt -3'      (SEQ ID NO: 9)

P4HA1:
Target sequence:
5'- AAGGATTTGTTGGGCATCCAG -3'      (SEQ ID NO: 10)

Sense siRNA:
5'- GGAUUUGUUGGGCAUCCAGtt -3'      (SEQ ID NO: 11)

Antisense siRNA:
5'- CUGGAUGCCCAACAAAUCCtt -3'      (SEQ ID NO: 12)

TXNIP
Target sequence:
5'- AAACAGACTTCGGAGTACCTG -3'      (SEQ ID NO: 13)

Sense siRNA:
5'- ACAGACUUCGGAGUACCUGtt -3'      (SEQ ID NO: 14)

Antisense siRNA:
5'- CAGGUACUCCGAAGUCUGUtt -3'      (SEQ ID NO: 15)
```

Double-stranded siRNA for selective silencing of thioredoxin was of the sequence GCAGAUCGAGAGCAA-GACUtt (SEQ ID NO:16). Scrambled (randomly arranged) RNAi (GUUGGCCAUUCUACUUCGCTTdtt (SEQ ID NO:17)) was used as negative control.

Double-stranded siRNA were transfected into cells (Lipofectamine2000 reagent, Invitrogen). 24 hours after transfection, HMVEC migration experiments were performed, in the presence of vehicle or stimuli. Cell migration and thioredoxin activity were assayed as described above.

Example 1

Identification of a Cholinergic Component of Growth Factor-Mediated Endothelial Cell Migration The effects of nicotine on human microvascular endothelial cell (HMVECs) migration were studied, using standard wounding migration assays.

FIG. 1, Panels A and B provide microphotographs showing in vitro model of HMVEC (EC)migration. These data show that, after wounding of the EC monolayer, EC migrate into the denuded area. As compared to ECs treated with vehicle (FIG. 1, Panel A) those treated with nicotine display greater migratory activity (FIG. 1, Panel B). Pictographs were taken at 200X from a Nikon TE-2000U Inverted microscope whose images are captured with a SPOT-RT CCD camera. Because of design constraints intrinsic to the camera, the images recorded represent a portion of the high-powered field of view.

Nicotine stimulated EC migration in a dose-dependent manner (FIG. 2A) with maximal stimulation at $10^{-8}$ M ($P<0.001$ vs control for $10^{-8}$ M nicotine). Stimulation with VEGF or bFGF also induced EC migration with maximal effects at 10 ng/ml. To further investigate the effects of nAChR-dependent pathways on EC migration, the effect of the nAChR antagonist, hexamethonium, on EC migration induced by nicotine, VEGF and bFGF was studied. Hexamethonium abrogated nicotine-induced EC migration (FIG. 2B). Unexpectedly, hexamethonium also attenuated the effect of the growth factors to increase EC migration (FIG. 2B). This effect was dose-dependent, and similar results were obtained with the nAChR antagonists mecamylamine ($10^{-6}$M) or α-bungarotoxin (10 ng/ml). The nAChR antagonist-regulated effects were not the result of cellular toxicity as addition of mecamylamine or hexamethonium alone did not induce cell death as examined via 3-[4,5-dimethylthiazol-2-yl]-2,5-diphenyl tetrazolium bromide (MTT) assays.

Figure 2B:
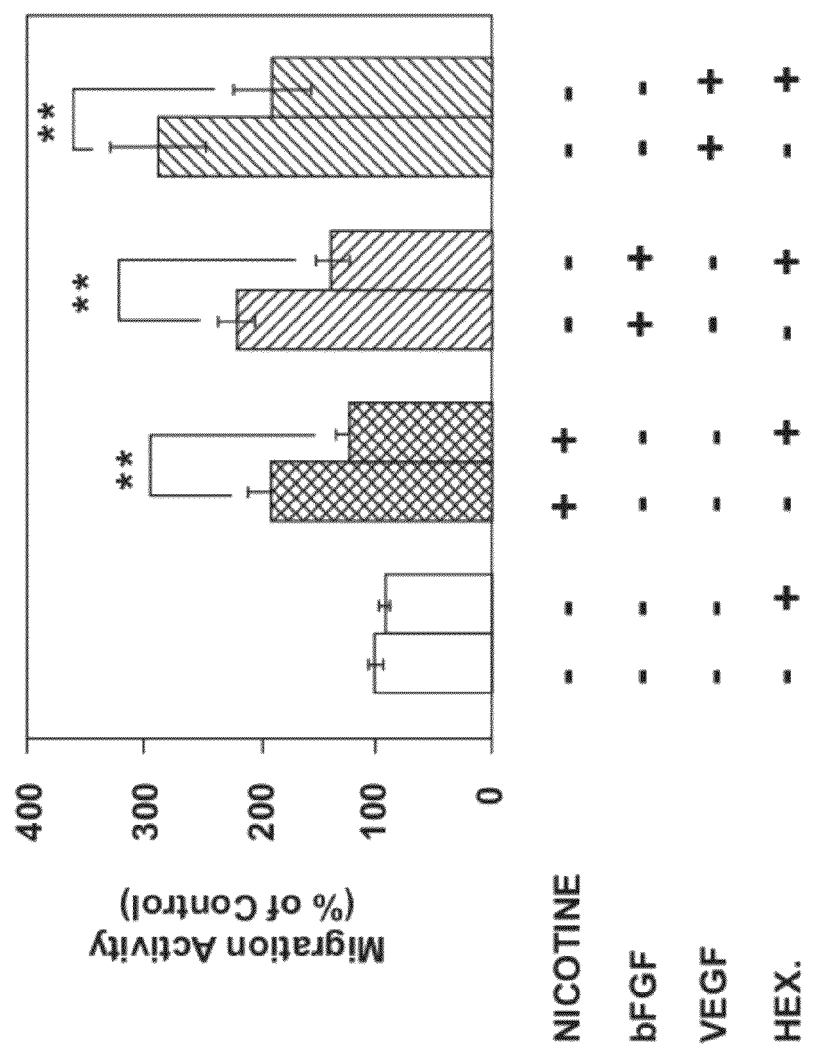

As shown in FIG. 2A, nicotine induced human microvascular endothelial cell (HMVEC) migration in a dose-dependent fashion, with maximal migration at $10^{-8}$ M nicotine (*$P<0.05$; $P<0.01$;*$P<0.001$). Values are expressed as a percentage of migrating cells per hpf in vehicle treated wells (basal value was 32±9 cells migrated into the denuded space at a magnification of 125×). All values are expressed as mean+/−SEM. As shown in FIG. 2B, nicotine ($10^{-8}$M)-induced migration is abrogated by HEX ($10^{-4}$M), the nAChR antagonist. Unexpectedly, HMVEC migration induced by VEGF or bFGF (10 ng/ml) is also significantly attenuated by HEX. (**$P<0.02$ for all stimuli vs angiogen+HEX; $P=0.07$ for Nicotine+Hex vs control+HEX; $P<0.05$ for either VEGF+HEX or bFGF+HEX Vs control+HEX). All values are expressed as mean+/−SEM Example 2

Identification of a Shared Transcriptional Response

Figure 3B:
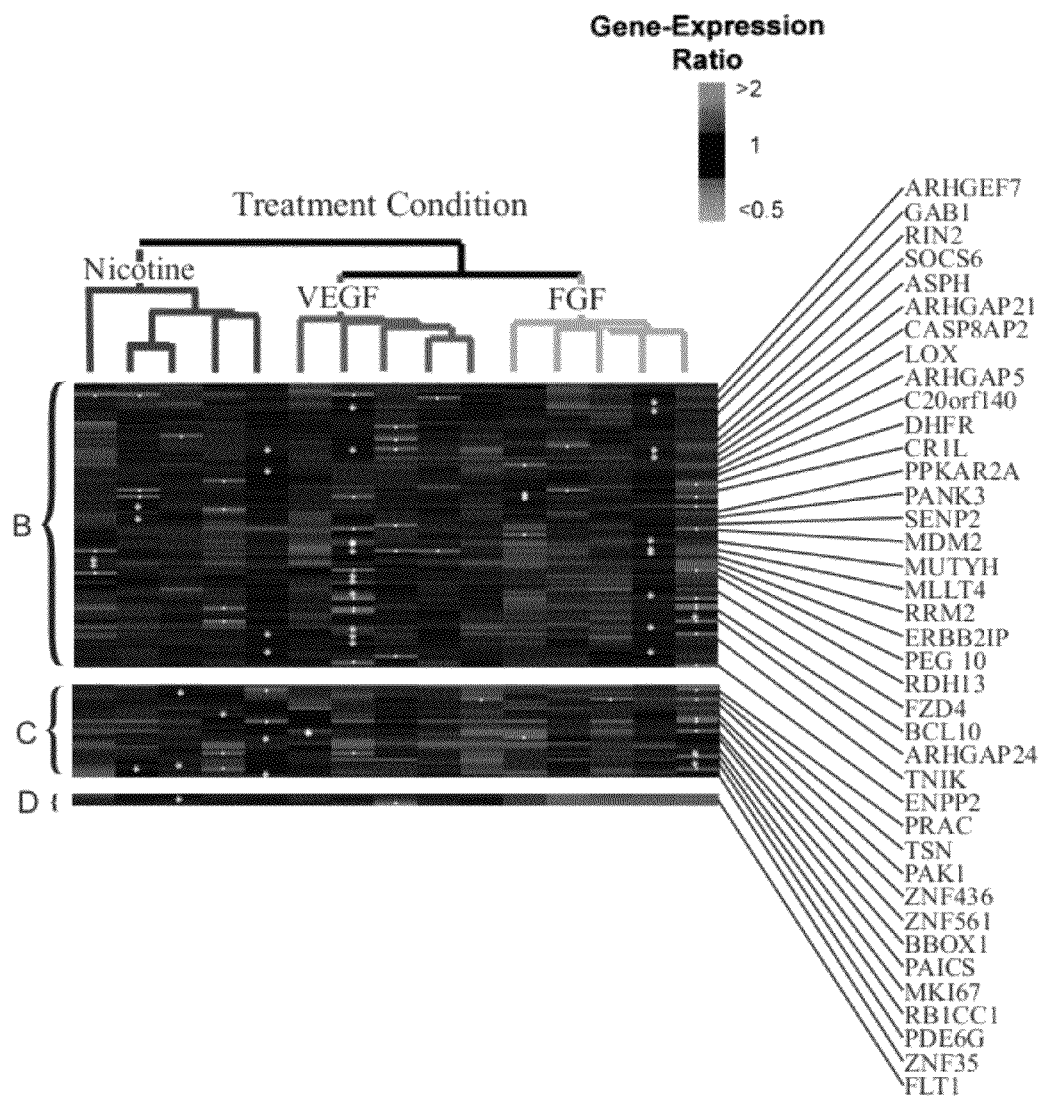

To confirm a cholinergic contribution to growth-factor induced EC migration, and to identify commonly regulated genes that may be required for HMVEC migration, microarray analysis of HMVECs was performed following exposure to nicotine, VEGF or bFGF. At 24 h post treatment, each of these stimuli induced profound transcriptional changes in HMVECs (FIGS. 3A-3C), resulting in differential expression of a total of 3072 genes uniquely identified by UniGene, as well as 312 expressed-sequence tags (ESTs), all of which were represented by 4070 nonredundant cDNA clones. To study relationships between gene expression programs induced by nicotine, VEGF or bFGF, data for all differentially expressed genes at 24 h were hierarchically clustered by gene and by array, thereby organizing genes and experimental samples on the basis of overall similarity of their gene expression patterns (FIG. 3A, Panel A, indicating relative positions of Panels B-D and Panels E-G re-presented in FIGS. 3B and 3C, respectively). The relationships between the transcriptional profiles at 24 h are summarized in a dendrogram (FIG. 3A, Panel A). All three stimuli induced distinct gene expression signatures which cluster within 3 distinct groups but there is a closer relationship between the VEGF- and bFGF-induced expression profiles, which cluster together on the same dendrogram branch.

Within the distinct transcriptional profiles induced by nicotine, VEGF or bFGF, 6 clusters with concordant gene expression were identified (3 clusters of commonly activated. and 3 commonly co-repressed genes; FIGS. 3B-3C, Panels B-F). The characteristics of these clusters provide some insights into shared cellular processes that may be requisite for angiogenic-induced cell migration.

The first activation cluster (FIG. 3B, Panel B), termed the "migration cluster", was enriched for genes associated with cytokinetic processes including migration-associated G-protein signaling (Rho GTPase regulatory proteins and RIN2), integrin binding (ERBB2IP and ADAM9), cell cycle regulation and proliferation (RRM2, MDM2, AHR, MLLT4 and MUTYH), NF-κB activation (BCL10 and CASP8AP2) and migration-associated oxidoreductase activity (LOX and ASPH). Significantly, three Rho GTPase activating proteins (GAPs) including ARHGAP5, ARHGAP21 and ARHGAP24 and one Rho guanine nucleotide exchange factors (GEF), ARHGEF7 were concordantly upregulated in this cluster. The small Rho GTPases (Cdc42 and Rac) play a central role in cell migration by regulating cytoskeletal remodelling and cellular adhesion. Rho GEFs and GAPs, by respectively controlling the activation and inactivation of small Rho GTPases, regulate the orchestration of cytoskeletal and adhesive changes during cytokinesis. Ridley et al. (2003) *Science* 302: 1704-1709. Of note, the p53 tumor suppressor protein, MDM2 is upregulated by each of the stimuli. Many other genes within the migration cluster are also implicated in oncogenesis (ADAM9, BCL10, MLLT4, MUTYH, ASPH).

A smaller second co-activation cluster (FIG. 3B, Panel C) includes the p21-activated kinase PAK1, an effector for the Rho GTPases Rac and Cdc42, that facilitates HMVEC migration by coordinating formation of new adhesions at the leading edge of the cell with contraction and detachment at the trailing edge. Other genes in this activation cluster comprise zinc finger proteins and genes involved in nucleic acid metabolism. Interestingly, all three stimuli induced activation of the VEGF receptor, FLT 1, an effect that was stronger for bFGF-treated cells than for nicotine or VEGF (FIG. 3B, Panel D—which contains a cluster of three nonredundant cDNA clones for FLT1). In addition to the co-induction of FLT1 by all three stimuli, it was found that several isoforms of nAChR subunits are upregulated by VEGF (Table 3). These results suggest potential synergistic interactions between VEGF and cholinergic signaling pathways.

TABLE 3

VEGF upregulates Acetylcholine Receptor Subunits (24 hr)

| Symbol | Name | Fold Change |
|---|---|---|
| CHRNB2 | Nicotinic receptor beta polypeptide 2 | 6.9 |
| CHRNB3 | Nicotinic receptor beta polypeptide 3 | 2.2 |
| CHRNA10 | Nicotinic receptor alpha polypeptide 10 | 2.0 |
| CHRM5 | Cholinergic muscarinic receptor 5 | 2.0 |
| CHRNA3 | Nicotinic receptor alpha polypeptide 3 | 1.7 |

The first repression cluster (FIG. 3C, Panel E) contains genes that are strongly downregulated by bFGF, many of which are also concordantly repressed by nicotine and VEGF, though to a lesser degree. A dominant theme amongst concordantly repressed genes is the downregulation of chemokine genes (principally of the CC class) involved leukocyte chemotaxis (CCL2, CCL7, CCL8, CCL20 and CX3CL).

Another prominent feature is the robust repression of thioredoxin interacting protein (TXNIP) (FIG. 3C, Panel E), a ubiquitous protein that binds and inhibits thioredoxin. Thioredoxin is a major intracellular antioxidant implicated in regulation of cell proliferation and angiogenesis.

Other co-repressed genes in this cluster have been implicated in apoptosis (TNFRSF1B, EP300), signal transduction (CD53, SQSTM1) and cell adhesion (ICAM1). The second repression cluster (FIG. 3C, Panel F) included two Ephrin receptors: EPHB4, a marker of venous differentiation and EPHA2, an inhibitor of cell migration which suppresses integrin function.

Other genes within this group were associated with tumor suppression, microtubular polymerization and signal transduction. The striking feature of the third cluster of co-repressed genes is a strong enrichment for metallothioneins (MT1E, MT1F, MT1G, MT1 L, MT1X, MT2A and MT3) (FIG. 3C, Panel G). Metallothioneins (MTs) comprise a superfamily of small cysteine-rich proteins with high affinity for metal ions and antioxidant activity. By serving as a cellular reservoir for zinc and copper, MTs regulate the function of proteins requiring these metals such as DNA and RNA polymerases, zinc finger transcription factors and p53. Hence downregulation of MTs by angiogenic agents is likely to significantly affect the activity of zinc and copper-dependent proteins. Other genes in this cluster are involved in diverse functions including cell proliferation/apoptosis (MYC, ERCC2), lipid transport (PTLP), calcium ion transport (CACNA1D) and actin binding (COTL1).

FIGS. 3A-C, Panels A-G provide a hierarchical cluster analysis of transcriptional effects of nicotine, VEGF or bFGF in human microvascular endothelial cells at 24 hours. FIG. 3A, Panel A shows an overview of the two way (genes against conditions) hierarchical cluster of 15 experiments (each condition was studied in quintuplicate to ensure reproducibility of data and to maximize the statistical validity of the data set) and 4070 non-redundant cDNA clones with significant change in expression at 24 hours. FIG. 3B, Panels B-D and FIG. 3C, Panels E-G show zoom boxes of concordantly expressed gene clusters, whose location are indicated by vertical bars adjacent to the dendrogram. Owing to space limitations, only genes discussed in the text are indicated by UniGene symbol. Data from individual elements or genes are represented in rows and experiments in columns. Red and green denote expression levels statistically significantly greater or less, respectively, than control values (in the absence of nicotine, VEGF, or bFGF, accordingly). Grey denotes technically inadequate or missing data. Chang et al. PLoS Biol. (2004 February) 2(2) E7. Epub 2004 Jan. 13. The intensity of the signal reflects the magnitude of the change from baseline. The dendrogram above the matrix represents similarities in patterns of expression between experimental samples.

Tables 1-2 provide a list of genes identified as being concordantly regulated in. response to stimulation of a call with nicotine, VEGF, or bFGF. Table 1 provides a representative list of genes identified as being concordantly regulated by nicotine, VEGF, and bFGF that, to the best of the inventor's knowledge, have not been previously reported to be related to angiogenesis. Table 2 provides a representative list of genes identified as being concordantly regulated by nicotine, VEGF, and bFGF, which genes have been implicated as having a role in angiogenesis (although, to the best of the inventor knowledge have not been previously identified as being concordantly regulated by nicotine, VEGF, and bFGF). "Expression" refers to whether the gene is concordantly down-regulated (and thus a concordantly-regulated anti-angiogenic gene, referred in the Table 1 as "down") or up-regulated (and thus a concordantly-regulated pro-angiogenic gene, referred in the Table 1 as "up") in expression in the presence of nicotine, VEGF, or bFGF relative to in the absence of these stimuli. "Chrom".indicates the chromosome position in the human genome. "Function" refers to the function or putative function assigned to the gene or gene product according to currently available databases.

It is to be understood that genes identified in Tables 1 and 2 as concordantly down-regulated in response to nicotine, VEGF, or bFGF are contemplated to be included as concordantly-regulated anti-angiogenic genes of the invention, while genes identified as concordantly up-regulated in response to nicotine, VEGF, or bFGF are contemplated are contemplated to be included as concordantly-regulated pro-angiogenic genes of the invention.

TABLE 1

Genes Identified as Relating to Angiogenesis

| Gene Name | Full Name | GenBank Accession | Unigene Accession | Chrom | Expression ("down" = concordantly-regulated anti-angiogenic gene: "up" = concordantly-regulated pro-angiogenic gene) | Function |
|---|---|---|---|---|---|---|
| ZNF200 | Zinc finger protein 200 | NM_198087 | AB209219 | 16p13.3 | down | could have a role in spermatogenesis, regulation of transcription |
| TXNIP | Thioredoxin interacting protein | NM_006472 | NM_006472 | 1q21.1 | down | molecular function unknown |
| RPS9 | Ribosomal protein S9 | NM_001013 | BF686617 | 19q13.4 | down | component of the 40S subunit of Ribosomes |
| RPL29 | Ribosomal protein L29 | NM_000992 | BM554029 | 3p21.3-p21.2 | down | a component of the 60S subunit of Ribosomes |
| RPL27A | Hypothetical protein MGC10850 | NM_000990 | AK125453 | 11p15 | down | a component of the 60S subunit of Ribosomes |
| RPL10 | Ribosomal protein L10 | NM_006013 | NM_006013 | Xq28 | down | a component of the 60S subunit of Ribosomes |
| PFKP | Phosphofructokinase, platelet | NM_002627 | AK126153 | 10p15.3-p15.2 | down | key control step of glycolysis |

TABLE 1-continued

Genes Identified as Relating to Angiogenesis

| Gene Name | Full Name | GenBank Accession | Unigene Accession | Chrom | Expression ("down" = concordantly-regulated anti-angiogenic gene: "up" = concordantly-regulated pro-angiogenic gene) | Function |
|---|---|---|---|---|---|---|
| MT2A | Metallothionein 2A | NM_005953 | BF131637 | 16q13 | down | Metal ion binding, copper ion homeostasis |
| MT1L | Metallothionein 1L | BG747999 | BG747999 | 16q13 | down | Metal ion binding |
| MT1F | Metallothionein IF | NM_005949 | BU742440 | 16q13 | down | bind various heavy metals |
| FLJ33706 | Hypothetical protein FLJ33706 | NM_182584 | NM_182584 | 20q11.21 | down | unknown |
| FLJ12442 | Hypothetical protein FLJ12442 | NM_022908 | AK091962 | 3p21.1 | down | unknown |
| FARSLA | Phenylalanine-tRNA synthetase-like, alpha subunit | NM_004461 | BC043565 | 19p13.2 | down | tRNA synthetase gene |
| CACNA1D | Calcium channel, voltage-dependent, L type, alpha 1D subunit | NM_000720 | M76558 | 3p14.3 | down | voltage-sensitive calcium channels |
| MT1E | metallothionein 1E | NM 175617 | Hs.534330 | 16q13 | down | Metal ion binding |
| MT1G | metallothionein 1G | NM 005950 | Hs.433391 | 16q13 | down | Metal ion binding |
| MT1X | metallothionein 1X | NM 005952 | Hs.374950 | 16q13 | down | Metal ion binding |
| MT3 | metallothionein 3 (growth inhibitory factor (neurotrophic)) | NM 005954 | Hs.73133 | 16q13 | down | Metal ion binding |
| EP300 | E1A binding protein p300 | NM_001429 | Hs.517517 | 22q13.2 | down | Metal ion binding |
| TAGLN | Transgelin | NM_001001522 | Hs.503998 | 11q23.2 | down | Muscle development |
| ERCC2 | excision repair cross-complementing rodent repair deficiency, complementation group 2 (xeroderma pigmentosum D) | NM_000400 | Hs.487294 | 19q13.3 | down | Induction of apoptosis |
| TIMM8B | translocase of inner mitochondrial membrane 8 homolog B (yeast) | NM_012459 | Hs.279915 | 11q23.1-q23.2 | down | Zinc ion binding |
| PLK2 | polo-like kinase 2 (*Drosophila*) | NM_006622 | Hs.398157 | 5q12.1-q13.2 | down | Regulation of I-kappaB kinase/NF-kappaB cascade |
| PSME2 | proteasome (prosome, macropain) activator subunit 2 (PA28 beta) | NM_002818 | Hs.434081 | 14q11.2 | down | Proteasome activator activity |
| PLTP | phospholipid transfer protein | NM_006227 | Hs.439312 | 20q12-q13.1 | down | Lipid transport |
| COTL1 | coactosin-like 1 (Dictyostelium) | NM_021149 | Hs.289092 | 16q24.1 | down | Actin binding |
| ZNF561 | zinc finger protein 561 | NM_152289 | AK122974 | 19p13.2 | up | Zinc finger protein, zinc iron binding |
| SOX17 | SRY (sex determining region Y)-box 17 | NM_022454 | AK025905 | 8q11.23 | up | regulation of embryonic development |
| SMC4L1 | SMC4 structural maintenance of chromosomes 4-like 1 (yeast) | NM_005496 | NM_005496 | 3q26.1 | up | Protein bining, cytokinesis |
| SLC7A2 | Solute carrier family 7 (cationic amino acid transporter, y+ system), member 2 | NM_003046 | NM_003046 | 8p22-p21.3 | up | transport of the cationic amino acids |
| RIN2 | Ras and Rab interactor 2 | NM_018993 | NM_018993 | 20 | up | membrane trafficking in the early endocytic pathway |
| PRAC | Small nuclear protein PRAC | NM_032391 | BG611169 | 17q21 | up | regulatory role in the nucleus |
| PCYOX1 | Prenylcysteine oxidase 1 | NM_016297 | AB020715 | 2p13.3 | up | degradation of prenylated proteins |
| P4HA1 | Procollagen-proline, 2-oxoglutarate 4-dioxygenase (proline 4-hydroxylase), alpha polypeptide I | NM_000917 | BX648829 | 10q21.3-q23.1 | up | Binding, oxidoreductase activity |
| LOC87769 | Hypothetical protein BC004360 | AK095850 | AK095850 | 13q32.3 | up | Hypothetical protein |
| K5B | Keratin 5b | NM_173352 | BX647095 | 12q13.13 | up | structure protein |
| FLJ12847 | Hypothetical protein | DQ043604 | DQ043604 | 8 | up | Hypothetical protein |
| CR1L | Complement component (3b/4b) receptor 1-like | XM_114735 | XM_114735 | 1q32.1 | up | Receptor activity |
| CASP8AP2 | CASP8 associated protein 2 | NM_012115 | AB037736 | 6q15 | up | apoptotic protein |
| ASPH | Aspartate beta-hydroxylase | NM_032468 | NM_032468 | 8q12.1 | up | calcium homeostasis, iron binding |
| ARHGEF7 | Rho guanine nucleotide exchange factor (GEF) 7 | NM_003899 | BX648030 | 13q34 | up | induce membrane ruffling |
| A2M | Alpha-2-macroglobulin | NM_000014 | CR749334 | 12p13.3-p12.3 | up | inhibits many proteases |
| GAB1 | GRB2-associated binding protein 1 | NM 002039 | Hs.80720 | 4q31.21 | up | Cell proliferation |
| SOCS6 | suppressor of cytokine signaling 6 | NM 004232 | Hs.44439 | 18q22.2 | up | Regulation of cell growth |
| C20orf140 | TBC 1 domain family, member 20 | NM 144628 | Hs.203514 | 20p13 | up | GTPase activator activity |
| CR1L | complement component (3b/4b) receptor 1-like | XP_114735 | Hs.149414 | 1q32.1 | up | Immune response |
| PANK3 | pantothenate kinase 3 | NM_024594 | Hs.388400 | 5q34 | up | Pantothenate kinase activity |
| SENP2 | SUMO1/sentrin/SMT3 specific peptidase 2 | NM_021627 | Hs.401388 | 3q27.2 | up | SUMO-specific protease activity |

TABLE 1-continued

Genes Identified as Relating to Angiogenesis

| Gene Name | Full Name | GenBank Accession | Unigene Accession | Chrom | Expression ("down" = concordantly-regulated anti-angiogenic gene: "up" = concordantly-regulated pro-angiogenic gene) | Function |
| --- | --- | --- | --- | --- | --- | --- |
| MUTYH | mutY homolog (*E. coli*) | NM_012222 | Hs.271353 | 1p34.3-p32.1 | up | DNA binding; Cell cycle |
| ERBB2IP | erbb2 interacting protein | NM_001006600; NM_018695 | Hs.519346 | 5q12.3 | up | Cell growth; Cell adhesion |
| PEG10 | paternally expressed 10 | XP_496907 | Hs.147492 | 7q21 | up | Apoptosis |
| RDH13 | retinol dehydrogenase 13 (all-trans and 9-cis) | NM_138412 | Hs.327631 | 19q13.42 | up | Oxidoreductase activity |
| BCL10 | B-cell CLL/lymphoma 10 | NM_003921 | Hs.193516 | 1p22 | up | Regulation of apoptosis |
| TSN | Translin | NM_004622 | Hs.75066 | 2q21.1 | up | DNA recombination |
| BBOX1 | butyrobetaine (gamma), 2-oxoglutarate dioxygenase (gamma-butyrobetaine hydroxylase) 1 | NM_003986 | Hs.144845 | 11p14.2 | up | Oxidoreductase activity |
| PAICS | phosphoribosylaminoimidazole carboxylase, phosphoribosylaminoimidazole succinocarboxamide synthetase | NM_006452 | Hs.518774 | 4pter-q21 | up | Phosphoribosylaminoimidazole carboxylase activity |
| MKI67 | antigen identified by monoclonal antibody Ki-67 | NM_002417 | Hs.80976 | 10q25-qter | up | Cell proliferation |
| RB1CC1 | RB1-inducible coiled-coil 1 | NM_014781 | Hs.196102 | 8p22-q21.13 | up | Cell cycle |
| PDE6G | phosphodiesterase 6G, cGMP-specific, rod, gamma | NM_002602 | Hs.1857 | 17q25 | up | cGMP-specific phosphodiesterase activity |

TABLE 2

Genes Previously Reported to Have a Role in Angiogenesis

| Gene Name | Full Name | GenBank Accession | Unigene Accession | Chrom | Expression ("down" = concordantly-regulated anti-angiogenic gene: "up" = concordantly-regulated pro-angiogenic gene) | Function |
| --- | --- | --- | --- | --- | --- | --- |
| ICAM1 | Intercellular adhesion molecule 1 (CD54) | NM_000201 | BC015969 | 19p13.3-p13.2 | down | binds to integrins of type CD11a/CD18 |
| HLA-G | HLA-G histocompatibility antigen | NM_002127 | AK093478 | 6p21.3 | down | Cellular defense response |
| GATA2 | GATA binding protein 2 | NM_032638 | AK127845 | 3q21.3 | down | Regulator of gene expression in hematopoietic cells |
| CCL20 | Chemokine (C—C motif) ligand 20 | NM_004591 | BG534134 | 2q33-q37 | down | chemotactic factor that attracts lymphocytes |
| CCL2 | Chemokine (C—C motif) ligand 2 | NM_002982 | BU570769 | 17q11.2-q21.1 | down | Protein amino acid phosphorylation, cell adhesion |
| MDM2 | Transformed 3T3 cell double minute 2, p53 binding protein (mouse) | NM_006881 | M92424 | 12q14.3-q15 | up | P53 binding protein |
| LOX | Lysyl oxidase | NM_002317 | NM_002317 | 5q23.2 | up | a role in tumor suppression. |
| FLT1 | Fms-related tyrosine kinase 1 (vascular endothelial growth factor/vascular permeability factor receptor) | NM_002019 | NM_002019 | 13q12 | up | receptor for VEGF |

Example 3

The Role of Thioredoxin Interacting Protein (TXNIP) The Cholinergic Contribution to Growth Factor-induced EC Migration The identification by hierarchical cluster analysis of commonly regulated genes revealed many genes heretofore not identified with EC migration or angiogenesis. Furthermore, as nAChR antagonism modulates VEGF- and bFGF-dependent EC migration, it was hypothesized that some of the concordant transcriptional effects may be nAChR-dependent. The downregulation by all three stimuli of thioredoxin interacting protein (TXNIP) was confirmed by RT-PCR (data not shown). TXNIP is an endogenous inhibitor of thioredoxin. TXNIP has not previously been shown to be involved in angiogenesis. The protein with which it interacts, thioredoxin, is a small ubiquitous redox protein that has been implicated in tumorigenesis and angiogenesis. Nishiyama et al. (1999) *J. Biol. Chem.* 274:21645-21650; and Baker et al. (1997) *Cancer Res.* 57:5162-5167. Thioredoxin is overexpressed in a wide variety of primary human tumors and overexpression of thioredoxin has been reported to increase tumor angiogenesis in a murine model. Welsh et al. (2002) *Cancer Res.* 62:5089-5095. Moreover, pharmacologic inhibition of thioredoxin signaling has been reported to inhibit tumor angiogenesis in a murine model using MCF-7 tumor xenografts. Welsh et al. (2003) *Mol. Cancer Ther.* 2:235-243 (20). Nevertheless, the role of TXNIP in angiogenesis (by modulating thioredoxin) has not been studied.

Figure 4:
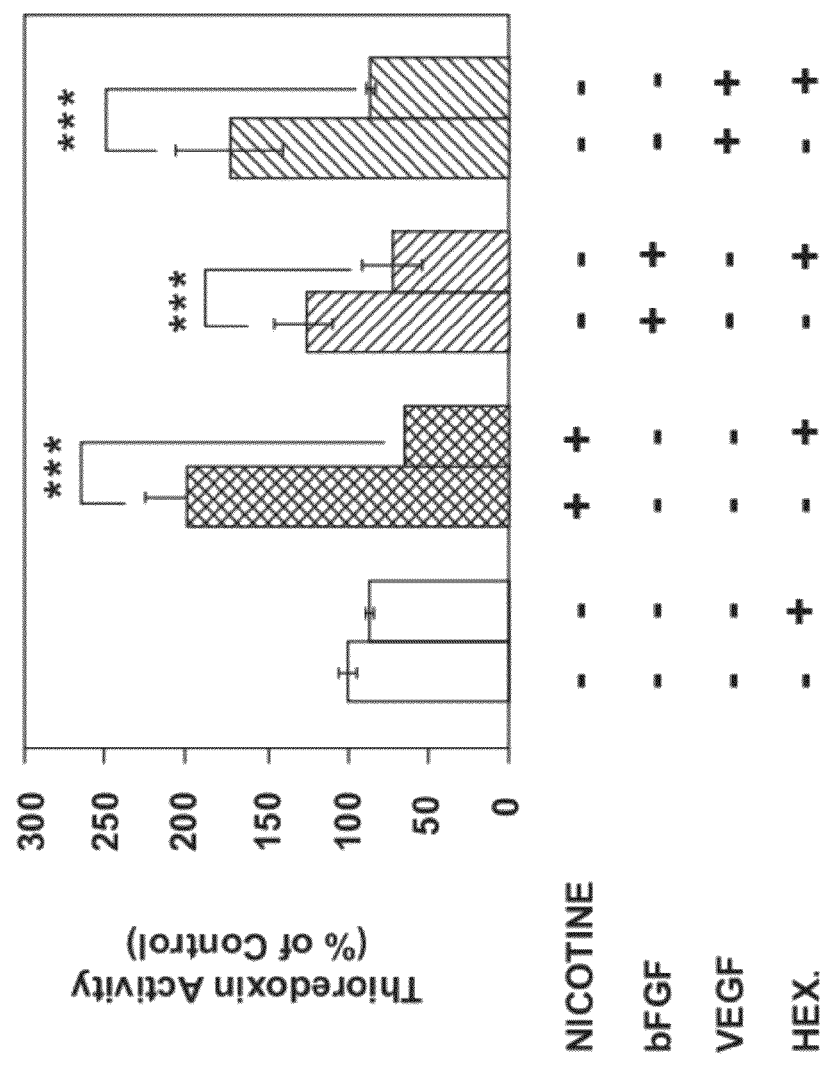
FIG. 4 depicts the role of the nAChR in the augmentation of thioredoxin activity by angiogenic growth factors.

Using a standard assay for thioredoxin activity (Wang et al. (2002) supra), it was found that addition of nicotine or VEGF induced HMVEC thioredoxin activity significantly above vehicle ($P<0.001$ vs. vehicle) (FIG. 4). The addition of bFGF induced a less robust ($P=0.02$ vs. vehicle) but significant increase in thioredoxin activity (FIG. 4). Notably, co-administration of hexamethonium inhibited nicotine-, VEGF- or bFGF-induced thioredoxin activity (FIG. 4) ($P<0.001$ for each stimulus vs stimulus+hexamethomium). Hexamethonium alone had no significant effect on thioredoxin activity.

Figure 5A:
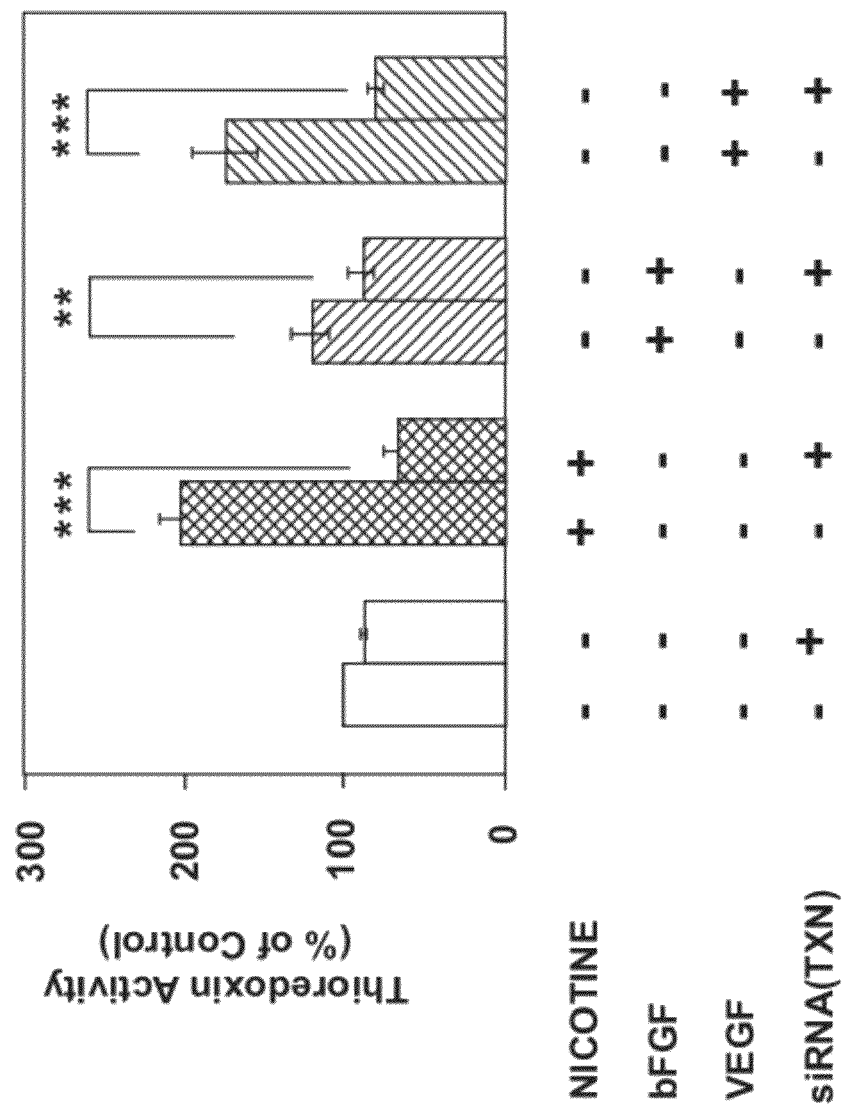
FIGS. 5A-5B depict the role of thioredoxin in endothelial cell migration induced by angiogenic growth factors.
Figure 5B:
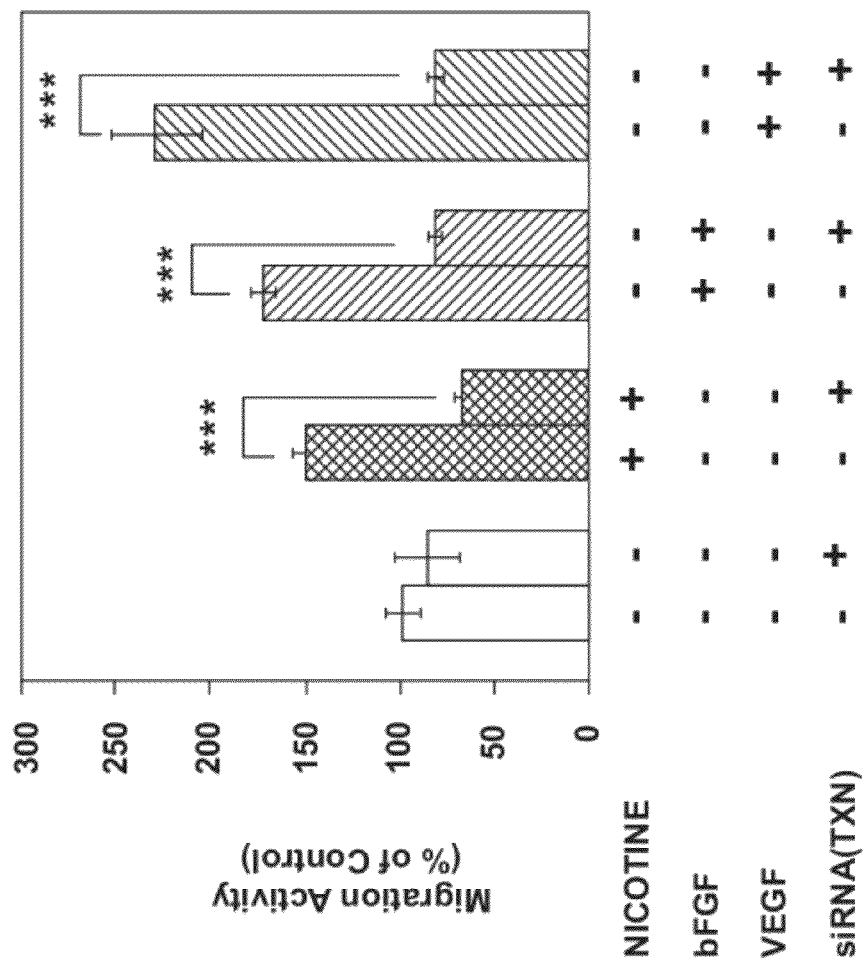

Transfection of small interference RNA (siRNA) against thioredoxin abrogated nicotine-, VEGF- or bFGF-induced thioredoxin activity (FIG. 5A) and, abolished cell migration induced by nicotine, VEGF or bFGF (FIG. 5B). Furthermore, in the absence of the stimuli, siRNA against TXNIP significantly stimulated thioredoxin activity ($P<0.0001$ vs. vehicle control) (FIG. 6 A), and strongly stimulated HMVEC migration (FIG. 6B, $P<0.0001$ vs. vehicle control). Of note, randomly arranged siRNA had no effect on thioredoxin activity or HMVEC migration.

FIG. 4 illustrates the role of the nicotinic acetylcholine receptor (nAChR) in augmentation by growth factors of thioredoxin activity. Nicotine ($10^{-8}$M), VEGF (10 ng/ml) or bFGF (10 ng/ml) each increased thioredoxin activity in human microvascular endothelial cells ($P<0.001$ for either nicotine or VEGF Vs control; $P=0.02$ for bFGF vs control). Notably, co-administration of the nAChR antagonist, hexamethonium ($10^{-4}$M), inhibited induction of thioredoxin activity by growth factors ($P<0.001$ for each stimulus vs stimulus+hexamethonium). Hexamethonium alone had no significant effect on thioredoxin activity ($P=0.08$). All experiments were conducted in hexiplicate. Values for thioredoxin activity are expressed as a percentage of control (vehicle-treated cells). All values are expressed as mean+/−SEM. ***$P<0.00$.

FIGS. 5A-B show that thioredoxin plays a critical role in endothelial cell migration. (FIG. 5A) Thioreduxin activity was increased by nicotine ($10^{-8}$M), VEGF (10 ng/ml) or bFGF (10 ng/ml) in human microvascular endothelial cells (HMVECs). These effects were blocked by short interference RNA (siRNA) against thioredoxin coding region. (*$P<0.001$; $P=0.01$). (FIG. 5B) HMVEC migration was increased by each of the stimuli, effects which were reversed by siRNA to thioredoxin. (***$P<0.001$). Of note, scrambled (randomly arranged) siRNA had no effect on thioredoxin activity or HMVEC migration (data not shown). All experiments were conducted in hexiplicate. Values for thioredoxin activity and migration are expressed as a percentage of control (vehicle-treated cells). All values are expressed as mean+/−SEM. Abbreviations include: siRNA—small interference RNA; TXN—thioredoxin.

Figure 6A:
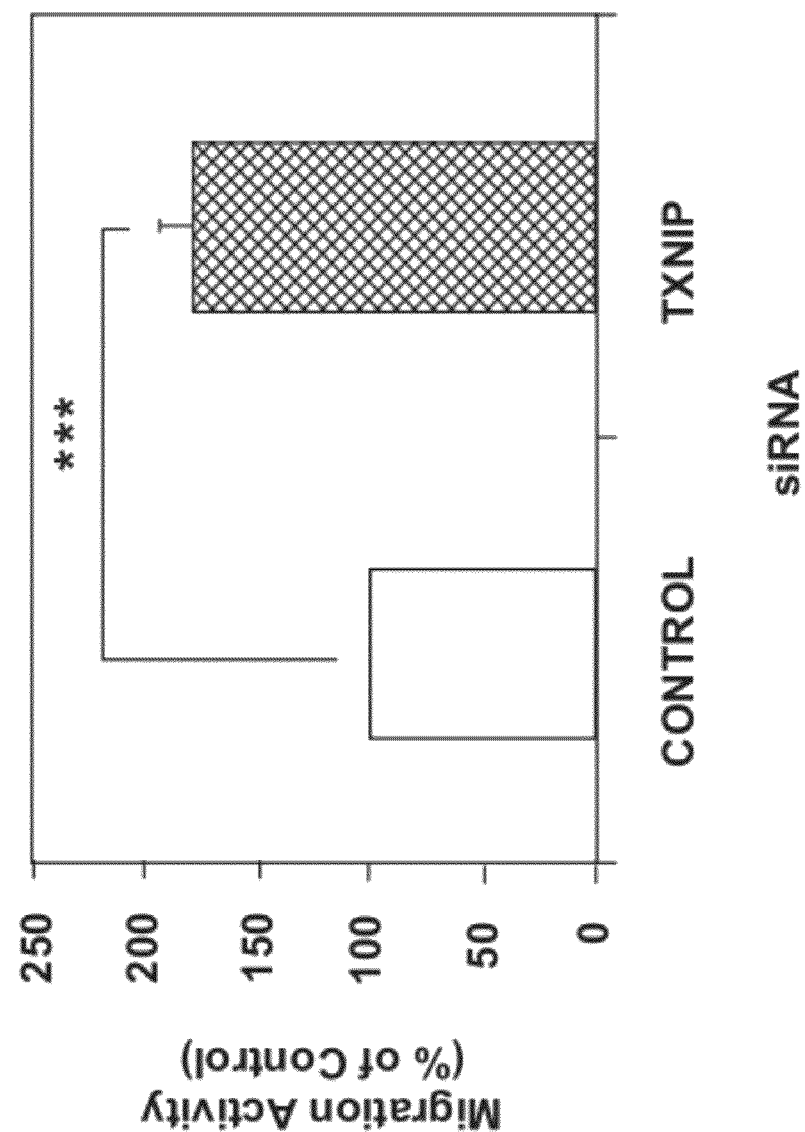

FIGS. 6A-B show that gene knockdown of thioredoxin interacting protein (TXNIP) induces human microvascular endothelial cell (HMVEC) migration. In the absence of added growth factors, small interference RNA (siRNA) against TXNIP significantly increased: (FIG. 6A) thioredoxin activity and (FIG. 6B) HMVEC migration. *** $P<0.0001$. Scrambled (randomly arranged) siRNA had no effect on thioredoxin activity or HMVEC migration. All experiments were conducted at least in triplicate. Values for thioredoxin activity and migration are expressed as a percentage of control (vehicle-treated cells). All values are expressed as mean+/−SEM.

Example 4

Inhibition of Expression of Gene Products Concordantly Up-Regulated in

Interference RNA technology was used to provide further evidence that the genes identified as being upregulated in the presence of each of VEGF, bFGF and nicotine are involved in angiogenesis. Three genes (ARHGEF, P4HA and Rin2) were selected from the set of upregulated genes. Double-stranded siRNA for selective silencing of ARHGEF, P4H4 or Rin2 were synthesized.

Figure 7:
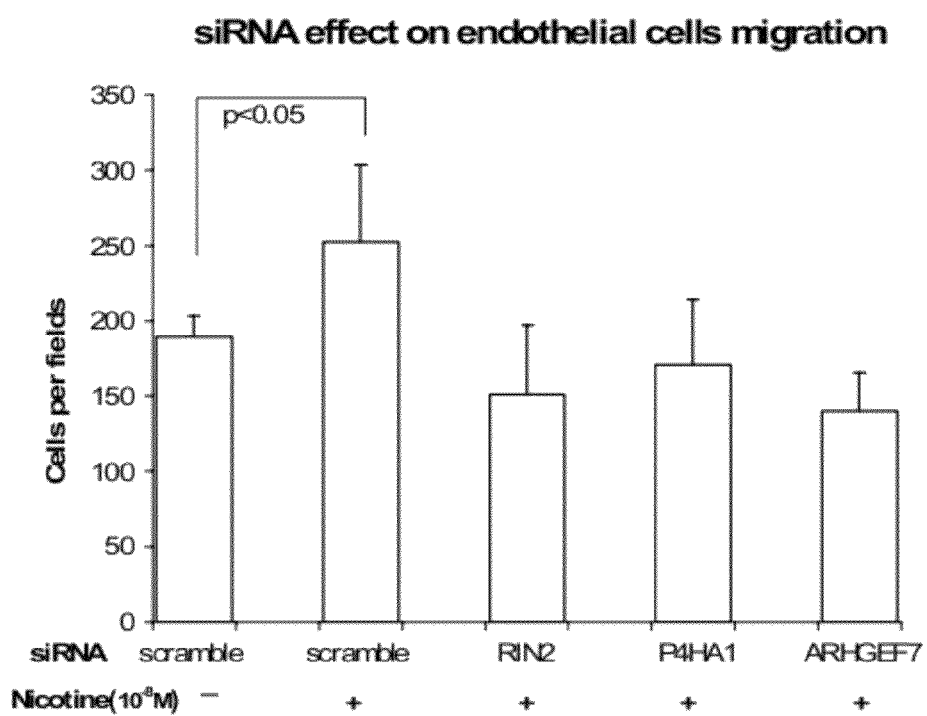
FIG. 7 is a graph showing the effect of inhibition of expression ARHGEF, P4HA or Rin2 genes on human microvascular endothelial cell (HMVEC) migration. A scrambled siRNA was used as a negative control.

Endothelial cells were transfected with one of the siRNA probes using lipofectamine, or were transfected with the corresponding scrambled siRNA probes. 96 hours after transfection, HMVEC migration experiments were performed as described above, in the presence of vehicle or stimuli. Cell migration was assayed as described above.

siRNA directed against ARHGEF, P4HA or Rin2 inhibited growth factor induced endothelial cell migration, whereas scrambled siRNA had no effect (FIG. 7). These data support a role for these genes in angiogenesis, and support the concept that the set of genes. concordantly upregulated by nicotine, VEGF or FGF will be involved in angiogenesis.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of stimulating therapeutic angiogenesis in an individual, the method comprising:
administering to the individual a short interfering nucleic acid that targets expression products of a TXNIP gene, in an amount sufficient to decrease expression of the TXNIP gene, wherein said administering provides for stimulation of angiogenesis in the individual, and wherein the individual has a condition amenable to treatment by stimulating therapeutic angiogenesis, and wherein the condition is a wound, an ulcer, a skin graft, a reattached limb, peripheral arterial disease, thromboangiitis obliterans, or stroke.

2. The method of claim 1, wherein said administering is effective to stimulate angiogenesis in or around a wound, in or around an ulcer, in or around a skin graft, in or around a transplanted tissue, or in or around a reattached limb.

3. The method of claim 1, wherein said administering is by a route selected from intravenous, intra-arterial, intra-pericardial, systemic, subcutaneous, intramuscular, inhalation, topical, and transdermal.

4. The method of claim 1, further comprising administering an angiogenic agent.

5. The method of claim 4, wherein the angiogenic agent is vascular endothelial growth factor.

* * * * *

UNITED STATES PATENT AND TRADEMARK OFFICE
CERTIFICATE OF CORRECTION

PATENT NO. : 8,236,772 B2
APPLICATION NO. : 11/521787
DATED : August 7, 2012
INVENTOR(S) : John P. Cooke It is certified that error appears in the above-identified patent and that said Letters Patent is hereby corrected as shown below:

In the Specification

Column 1, line 16-18, Statement Regarding Federally Sponsored Research should read --This invention was made with Government support under contract CA098303 awarded by the National Institutes of Health. The Government has certain rights in this invention.--

Signed and Sealed this
Fourth Day of June, 2013

Teresa Stanek Rea
*Acting Director of the United States Patent and Trademark Office*

SEQUENCE LISTING

<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
agatcaggtc taagcagcag aaca                                              24

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
tcagatctac ccaactcatc tcaga                                             25

<210> SEQ ID NO 3
<211> LENGTH: 20
<212> TYPE: DNA
<213> ORGANISM: Artificial Sequence
<220> FEATURE:
<223> OTHER INFORMATION: probe

<400> SEQUENCE: 3
ccagcatggc cagccgaacc                                                   20

<210> SEQ ID NO 4
<211> LENGTH: 21
<212> TYPE: DNA
<213> ORGANISM: human

<400> SEQUENCE: 4
aagcctgtgt ctcccaaatc a                                                 21

<210> SEQ ID NO 5
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 5
gccugugucu cccaaaucat t                                                 21

<210> SEQ ID NO 6
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 6
ugauuuggga gacacaggct t                                                 21

<210> SEQ ID NO 7
<211> LENGTH: 21
<212> TYPE: DNA
<213> ORGANISM: human

-continued

```
<400> SEQUENCE: 7
aactgaaaca ggagatggtg c                                              21

<210> SEQ ID NO 8
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 8
cugaaacagg agauggugct t                                              21

<210> SEQ ID NO 9
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 9
gcaccaucuc cuguuucagt t                                              21

<210> SEQ ID NO 10
<211> LENGTH: 21
<212> TYPE: DNA
<213> ORGANISM: human

<400> SEQUENCE: 10
aaggatttgt tgggcatcca g                                              21

<210> SEQ ID NO 11
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 11
ggauuuguug ggcauccagt t                                              21

<210> SEQ ID NO 12
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 12
cuggaugccc aacaaaucct t                                              21

<210> SEQ ID NO 13
<211> LENGTH: 21
<212> TYPE: DNA
<213> ORGANISM: human

<400> SEQUENCE: 13
aaacagactt cggagtacct g                                              21

<210> SEQ ID NO 14
<211> LENGTH: 21
<212> TYPE: DNA
<213> ORGANISM: Artificial Sequence
<220> FEATURE:
<223> OTHER INFORMATION: combined DNA/RNA sequence
```

```
<400> SEQUENCE: 14
acagacuucg gaguaccugt t                                              21

<210> SEQ ID NO 15
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 15
cagguacucc gaagucugut t                                              21

<210> SEQ ID NO 16
<211> LENGTH: 21
<212> TYPE: DNA
<213> ORGANISM: Artificial Sequence
<220> FEATURE:
<223> OTHER INFORMATION: combined DNA/RNA sequence

<400> SEQUENCE: 16
gcagaucgag agcaagacut t                                              21

<210> SEQ ID NO 17
<211> LENGTH: 24
<212> TYPE: DNA
<213> ORGANISM: Artificial Sequence
<220> FEATURE:
<223> OTHER INFORMATION: combined DNA/RNA sequence

<400> SEQUENCE: 17
guuggccauu cuacuucgct tdtt                                           24
```